(12) United States Patent
Shan et al.

(10) Patent No.: US 12,268,487 B2
(45) Date of Patent: Apr. 8, 2025

(54) ELECTRONIC DEVICE, METHOD FOR CONTROLLING ELECTRONIC DEVICE TO PERFORM PPG DETECTION, AND MEDIUM

(71) Applicant: Huawei Technologies Co., Ltd., Shenzhen (CN)

(72) Inventors: Xiaocai Shan, Shenzhen (CN); Hongbao Li, Shenzhen (CN); Yixin Chen, Shenzhen (CN); Jie Zhang, Shenzhen (CN); Xi Huang, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 434 days.

(21) Appl. No.: 17/790,900

(22) PCT Filed: Dec. 30, 2020

(86) PCT No.: PCT/CN2020/141584
§ 371 (c)(1),
(2) Date: Jul. 5, 2022

(87) PCT Pub. No.: WO2021/139588
PCT Pub. Date: Jul. 15, 2021

(65) Prior Publication Data
US 2023/0045200 A1 Feb. 9, 2023

(30) Foreign Application Priority Data
Jan. 6, 2020 (CN) .......................... 202010009395.7

(51) Int. Cl.
*A61B 5/024* (2006.01)
*A61B 5/00* (2006.01)
(Continued)

(52) U.S. Cl.
CPC ........ *A61B 5/02416* (2013.01); *A61B 5/7221* (2013.01); *A61B 5/7275* (2013.01);
(Continued)

(58) Field of Classification Search
USPC .......................................... 702/189
See application file for complete search history.

(56) References Cited

U.S. PATENT DOCUMENTS 6,319,205 B1 11/2001 Goor et al.
8,617,080 B2 12/2013 Turcott
(Continued)

FOREIGN PATENT DOCUMENTS

CN 102165698 A 8/2011
CN 103327886 A 9/2013
(Continued)

OTHER PUBLICATIONS

Yizhou, Z., "A Wearable Multi-physiological Signs Acquisition System Based on Photoplethvsmogram," Master"s Dissertation, Zhejiang University, Mar. 2017, 82 pages (with an English Abstract).
(Continued)

*Primary Examiner* — Paul D Lee
(74) *Attorney, Agent, or Firm* — SLATER MATSIL, LLP

(57) ABSTRACT

This application discloses a method for controlling an electronic device to perform photoplethysmography detection. The method includes obtaining historical detection data of a photoplethysmography sensor, calculating a confidence of the historical detection data, determining, based on the calculated confidence of the historical detection data, whether a light source to be turned on by the photoplethysmography sensor in a next detection time segment includes a light source different from a light source turned on when the historical detection data is obtained, and determining that a photoelectric sensing element to be turned on in the
(Continued)

next detection time segment is a photoelectric sensing element corresponding to the determined light source to be turned on.

20 Claims, 15 Drawing Sheets

(51) Int. Cl.
 *G16H 10/60* (2018.01)
 *A61B 5/02* (2006.01)
(52) U.S. Cl.
 CPC ........... *A61B 5/7282* (2013.01); *G16H 10/60* (2018.01); *A61B 5/02* (2013.01); *A61B 5/02438* (2013.01); *A61B 2560/0209* (2013.01)

(56) References Cited

U.S. PATENT DOCUMENTS

| | | | |
|---|---|---|---|
| 9,538,927 B2 | 1/2017 | Thaveeprungsriporn et al. | |
| 9,668,698 B2 | 6/2017 | Schipper | |
| 9,675,281 B2 | 6/2017 | Arnold et al. | |
| 10,405,761 B2 | 9/2019 | Ouwerkerk et al. | |
| 10,682,083 B2 | 6/2020 | Jelfs et al. | |
| 10,842,394 B2 | 11/2020 | Church et al. | |
| 10,939,873 B2 | 3/2021 | Garudadri et al. | |
| 11,134,855 B2 | 10/2021 | Yuan | |
| 11,197,620 B2 | 12/2021 | Huang | |
| 11,422,818 B2 | 8/2022 | Ma | |
| 2013/0324809 A1* | 12/2013 | Lisogurski | A61B 5/7285 600/323 |
| 2015/0065889 A1 | 3/2015 | Gandelman et al. | |
| 2015/0223700 A1 | 8/2015 | Kirenko | |
| 2015/0282724 A1 | 10/2015 | McDuff et al. | |
| 2015/0371028 A1 | 12/2015 | Patel et al. | |
| 2016/0324432 A1 | 11/2016 | Ahmed et al. | |
| 2017/0014040 A1 | 1/2017 | Shim et al. | |
| 2017/0311825 A1 | 11/2017 | Weekly et al. | |
| 2018/0125418 A1 | 5/2018 | Haakma et al. | |
| 2018/0279956 A1* | 10/2018 | Waydo | A61B 5/02433 |
| 2018/0344178 A1 | 12/2018 | Deng et al. | |
| 2019/0090757 A1 | 3/2019 | Xiao et al. | |
| 2019/0192079 A1 | 6/2019 | Groenendaal et al. | |
| 2019/0374117 A1 | 12/2019 | Liao | |
| 2021/0330207 A1* | 10/2021 | Richards | A61B 5/0059 |
| 2022/0218279 A1 | 7/2022 | Yang et al. | |
| 2022/0248968 A1 | 8/2022 | Xi et al. | |

FOREIGN PATENT DOCUMENTS

| | | |
|---|---|---|
| CN | 104688202 A | 6/2015 |
| CN | 105592780 A | 5/2016 |
| CN | 105813565 A | 7/2016 |
| CN | 105816163 A | 8/2016 |
| CN | 106333657 A | 1/2017 |
| CN | 205901870 U | 1/2017 |
| CN | 107432741 A | 12/2017 |
| CN | 107661094 A | 2/2018 |
| CN | 107708528 A | 2/2018 |
| CN | 107735019 A | 2/2018 |
| CN | 108652605 A | 10/2018 |
| CN | 109144214 A | 1/2019 |
| CN | 109189207 A | 1/2019 |
| CN | 109195510 A | 1/2019 |
| CN | 110367946 A | 10/2019 |
| CN | 110393514 A | 11/2019 |
| CN | 110432883 A | 11/2019 |
| JP | 2018505737 A | 3/2018 |
| KR | 20170008043 A | 1/2017 |
| WO | 2015134654 A1 | 9/2015 |
| WO | 2017202120 A1 | 11/2017 |

OTHER PUBLICATIONS

Zhou, Y. et al., "Design of Reflective PPG Signal Based on Photoplethysmography," Chengdu University of Technology, Electronic World, Electronic World, Editorial Mailbox, No. 12, 2016, 2 pages (with English Abstract).

* cited by examiner

ELECTRONIC DEVICE, METHOD FOR CONTROLLING ELECTRONIC DEVICE TO PERFORM PPG DETECTION, AND MEDIUM

CROSS-REFERENCE TO RELATED APPLICATIONS

This application is a National Stage of International Application No. PCT/CN2020/141584, filed on Dec. 30, 2020, which claims priority to Chinese Patent Application No. 202010009395.7, filed on Jan. 6, 2020, both of which are hereby incorporated by reference in their entireties.

TECHNICAL FIELD

This application relates to the field of communications technologies, and in particular, to an electronic device, a method for controlling an electronic device to perform PPG detection, and a medium.

BACKGROUND

A photoplethysmography (Photo Plethysmo Graphy, PGG) technology is used to develop a small and wearable pulse sensor. The pulse sensor system includes a red, infrared, or green light emitting diode and a photoelectric detector, and provides a simple, reliable, and low-cost non-invasive pulse rate monitoring method. A principle of a PPG sensor is to optically detect a fluctuation change of a blood volume in a tissue microvascular bed under a systolic or diastolic effect of the heart. For example, when the heart is systolic, if a blood volume of the tissue increases and a light absorption amount increases, light intensity detected by the photoelectric detector is relatively low; or when the heart is diastolic, if a blood volume of the tissue decreases and a light absorption amount decreases, light intensity detected by the photoelectric detector is relatively high.

Because a change of light intensity of the PPG sensor is related to a slight change of hemoperfusion of the tissue, the PPG sensor may be used to provide information about a cardiovascular system, for example, physiological parameter information such as blood pressure information, blood sample information, pulse rate information, and respiratory rate information, to track a health status of a user.

SUMMARY

Embodiments of this application provide a method for controlling an electronic device to perform photoplethysmography detection and a medium, so that turn-on and turn-off of a photoelectric sensing element can be dynamically adjusted based on a confidence of historical detection data of a photoplethysmography sensor. This can ensure a detection result confidence and reduce power consumption.

According to a first aspect, an embodiment of this application provides a method for controlling an electronic device to perform photoplethysmography detection. The electronic device includes a photoplethysmography sensor, the photoplethysmography sensor includes a plurality of light sources and at least one photoelectric sensing element, and each light source has a corresponding photoelectric sensing element. The method includes: obtaining historical detection data of the photoplethysmography sensor; calculating a confidence of the historical detection data; determining, based on the calculated confidence of the historical detection data, whether a light source to be turned on by the photoplethysmography sensor in a next detection time segment includes a light source different from a light source turned on when the historical detection data is obtained; and determining that a photoelectric sensing element to be turned on in the next detection time segment is a photoelectric sensing element corresponding to the determined light source to be turned on. That is, the light source to be turned on in the next detection time segment is determined based on a confidence of collected data of the current light source.

In a possible implementation of the first aspect, the obtaining historical detection data of the photoplethysmography sensor includes: obtaining detection data detected by the photoplethysmography sensor in a detection time segment closest to the next detection time segment. The data in the detection time segment closest to the next detection time segment can be better referenced than data in a detection time segment farther from the next detection time segment. Therefore, a confidence calculation result of the data in the detection time segment closest to the next detection time segment is more reliable.

In a possible implementation of the first aspect, the calculating a confidence of the historical detection data includes: calculating, based on the historical detection data, a probability that a detected event occurs to a user of the electronic device; and calculating the confidence of the historical detection data based on the probability that the detected event occurs to the user, where if the probability that the detected event occurs to the user is closer to 0 or 1, the confidence is higher.

In a possible implementation of the first aspect, the calculating, based on the historical detection data, a probability that a detected event occurs to a user of the electronic device includes: calculating, by using the following formulas, the probability that the detected event occurs to the user:

$p=1/(1+e^{\wedge}(-\alpha^{\wedge} Tf))$; and $c=2 \times \text{abs}(0.5-p)$.

Herein, c is a confidence calculation result; f is a feature related to atrial fibrillation detection; α is a weight matrix corresponding to the feature related to atrial fibrillation detection; e is the base of the natural logarithm; and p represents a possibility that the data is atrial fibrillation.

In a possible implementation of the first aspect, the determining, based on the calculated confidence of the historical detection data, whether a light source to be turned on by the photoplethysmography sensor in a next detection time segment includes a light source different from a light source turned on when the historical detection data is obtained includes: determining whether the confidence of the historical detection data is greater than a predetermined threshold; and when determining that the confidence is greater than the predetermined threshold, determining that the light source to be turned on by the photoplethysmography sensor in the next detection time segment includes only the light source turned on when the historical detection data is obtained; or when determining that the confidence is not greater than the predetermined threshold, determining that the light source to be turned on by the photoplethysmography sensor in the next detection time segment includes the light source turned on when the historical detection data is obtained and the different light source. That is, when the confidence of the data of the current light source is greater than or equal to a predetermined threshold, it is considered that the confidence of the current light source is high. In this case, the current light source may still be used in the next detection time segment. Alternatively, when the confidence of the data of the current light source is less than the predetermined threshold, it is considered that the confidence of the current light source is low. In this case, another light source is turned on in the next detection time segment to collect light source data and calculate a light source data confidence.

In a possible implementation of the first aspect, the method further includes: obtaining regular information, where the regular information includes at least one of user information, motion information, and a current measurement time of the electronic device, and the user information includes at least one of physical health information, age information, and gender information of the user. The regular information of the user such as the health information may be used to further determine a specific physical condition of the user, to further determine a quantity of light sources to be turned on.

In a possible implementation of the first aspect, the determining, based on the calculated confidence of the historical detection data, whether a light source to be turned on by the photoplethysmography sensor in a next detection time segment includes a light source different from a light source turned on when the historical detection data is obtained includes: determining, based on the regular information and the confidence of the historical detection data, whether the light source to be turned on by the photoplethysmography sensor in the next detection time segment includes the light source different from the light source turned on when the historical detection data is obtained.

In a possible implementation of the first aspect, the method further includes: determining whether an initialization condition of the photoplethysmography sensor is met; and determining, based on the regular information when the initialization condition is met, an initial light source and an initial photoelectric sensing element that are to be turned on by the photoplethysmography sensor. The initialization condition of the photoplethysmography sensor is determined by using the regular information. The light source to be turned on in the next detection time segment is determined based on a confidence of light source data of a default light source turned on by an initialized PPG sensor.

In a possible implementation of the first aspect, the initialization condition includes any one of the following: The electronic device is used by the user for the first time. A time point for switching between a day mode and a night mode of the photoplethysmography sensor is reached. The electronic device performs data update. To be specific, when the user performs registration and login for the first time, the PPG sensor is initialized. Because a motion status or a physical condition of the user during the day is different from that during the night, PPG light source data required during the day is also different from that required during the night. Therefore, in the foregoing two time segments, the PPG sensor performs switching between quantities of light sources, to reduce power consumption as much as possible.

In a possible implementation of the first aspect, the determining, based on the regular information when the initialization condition is met, an initial light source and an initial photoelectric sensing element that are to be turned on by the photoplethysmography sensor includes: calculating, by using the following formulas, a quantity of initial light sources to be turned on by the photoplethysmography sensor:

$$r = 1/(1+e^{\wedge}(-\theta^{\wedge}Tx)); \text{ and}$$

$$b = \text{Ceil}(r \times n), \text{ where}$$

r represents a health risk, and a higher value of r indicates a higher health risk of the user; the vector x represents a health risk parameter; $\theta$ is a matrix, and represents a weight of impact of the health risk parameter on health; e is the base of the natural logarithm; b represents the calculated quantity of light sources to be turned on; and n represents a maximum quantity of light sources supported by the device; and determining that the initial photoelectric sensing element to be turned on is a photoelectric sensing element corresponding to the determined initial light source to be turned on.

According to a second aspect, an embodiment of this application provides a method for controlling an electronic device to perform photoplethysmography detection. A second electronic device includes a photoplethysmography sensor, the photoplethysmography sensor includes a plurality of light sources and at least one photoelectric sensing element, and each light source has a corresponding photoelectric sensing element.

The method includes: A first electronic device obtains historical detection data of the photoplethysmography sensor from the second electronic device. The first electronic device calculates a confidence of the historical detection data. The first electronic device determines, based on the calculated confidence of the historical detection data, whether a light source to be turned on by the photoplethysmography sensor of the second electronic device in a next detection time segment includes a light source different from a light source turned on when the historical detection data is obtained. The first electronic device determines that a photoelectric sensing element to be turned on by the photoplethysmography sensor of the second electronic device in the next detection time segment is a photoelectric sensing element corresponding to the determined light source to be turned on. The first electronic device sends, to the second electronic device, information about the light source to be turned on and information about the photoelectric sensing element to be turned on.

For example, the first electronic device is a mobile phone, and the second electronic device is a band. Specifically, the mobile phone obtains user data on the band or user data for registration and login on the mobile phone, to control initialization of a light source of a PPG sensor on the band, turn-on of a light source channel, data collection, and calculation of a confidence of light source data.

In a possible implementation of the second aspect, that a first electronic device obtains historical detection data of the photoplethysmography sensor from the second electronic device includes:

obtaining detection data detected by the photoplethysmography sensor in a detection time segment closest to the next detection time segment.

In a possible implementation of the second aspect, that the first electronic device calculates a confidence of the historical detection data includes:

The first electronic device calculates, based on the historical detection data, a probability that a detected event occurs to a user of the electronic device. The first electronic device calculates the confidence of the historical detection data based on the probability that the detected event occurs to the user, where if the probability that the detected event occurs to the user is closer to 0 or 1, the confidence is higher.

In a possible implementation of the second aspect, that the first electronic device calculates, based on the historical detection data, a probability that a detected event occurs to a user of the electronic device includes calculating, by using the following formulas, the probability that the detected event occurs to the user:

$p=1/(1+e^{\wedge}(-\alpha^{\wedge}Tf))$; and $c=2\times abs(0.5-p)$.

Herein, c is a confidence calculation result; f is a feature related to atrial fibrillation detection; α is a weight matrix corresponding to the feature related to atrial fibrillation detection; e is the base of the natural logarithm; and p represents a possibility that the data is atrial fibrillation.

In a possible implementation of the second aspect, that the first electronic device determines, based on the calculated confidence of the historical detection data, whether a light source to be turned on by the photoplethysmography sensor in a next detection time segment includes a light source different from a light source turned on when the historical detection data is obtained includes:

The first electronic device determines whether the confidence of the historical detection data is greater than a predetermined threshold.

When determining that the confidence is greater than the predetermined threshold, the first electronic device determines that the light source to be turned on by the photoplethysmography sensor in the next detection time segment includes only the light source turned on when the historical detection data is obtained.

Alternatively, when determining that the confidence is not greater than the predetermined threshold, the first electronic device determines that the light source to be turned on by the photoplethysmography sensor in the next detection time segment includes the light source turned on when the historical detection data is obtained and the different light source.

In a possible implementation of the second aspect, the method further includes: The first electronic device obtains regular information, where the regular information includes at least one of user information, motion information, and a current measurement time of the electronic device, and the user information includes at least one of physical health information, age information, and gender information of the user.

In a possible implementation of the second aspect, that the first electronic device determines, based on the calculated confidence of the historical detection data, whether a light source to be turned on by the photoplethysmography sensor in a next detection time segment includes a light source different from a light source turned on when the historical detection data is obtained includes:

The first electronic device determines, based on the regular information and the confidence of the historical detection data, whether the light source to be turned on by the photoplethysmography sensor in the next detection time segment includes the light source different from the light source turned on when the historical detection data is obtained.

In a possible implementation of the second aspect, the method further includes: The first electronic device determines whether an initialization condition of the photoplethysmography sensor is met. The first electronic device determines, based on the regular information when the initialization condition is met, an initial light source and an initial photoelectric sensing element that are to be turned on by the photoplethysmography sensor.

In a possible implementation of the second aspect, the initialization condition includes any one of the following: The electronic device is used by the user for the first time. A time point for switching between a day mode and a night mode of the photoplethysmography sensor is reached. The electronic device performs data update.

In a possible implementation of the second aspect, that the first electronic device determines, based on the regular information when the initialization condition is met, an initial light source and an initial photoelectric sensing element that are to be turned on by the photoplethysmography sensor includes: calculating, by using the following formulas, a quantity of initial light sources to be turned on by the photoplethysmography sensor:

$r=1/(1+e^{\wedge}(-\theta Tx))$; and $b=\text{Ceil}(r\times n)$, where r represents a health risk, and a higher value of r indicates a higher health risk of the user; the vector x represents a health risk parameter; θ is a matrix, and represents a weight of impact of the health risk parameter on health; e is the base of the natural logarithm; b represents the calculated quantity of light sources to be turned on; and n represents a maximum quantity of light sources supported by the device; and determining that the initial photoelectric sensing element to be turned on is a photoelectric sensing element corresponding to the determined initial light source to be turned on.

According to a third aspect, an embodiment of this application provides a machine-readable medium. The machine-readable medium stores instructions, and when the instructions are executed on a machine, the machine is enabled to perform the method for controlling an electronic device to perform photoplethysmography detection in any one of the foregoing aspects.

According to a fourth aspect, an embodiment of this application provides an electronic device, including: one or more processors; a memory, configured to store instructions; and a photoplethysmography sensor. The photoplethysmography sensor includes a plurality of light sources and at least one photoelectric sensing element, and each light source has a corresponding photoelectric sensing element. When the instructions are executed by the one or more processors, the electronic device is enabled to control the photoplethysmography sensor to perform the method for controlling an electronic device to perform photoplethysmography detection in any one of the foregoing aspects.

According to a fifth aspect, an embodiment of this application provides an electronic device, including: one or more processors; and a memory, configured to store instructions. When the instructions are executed by the one or more processors, the electronic device is enabled to perform the method for controlling an electronic device to perform photoplethysmography detection in any one of the foregoing aspects.

According to a sixth aspect, an embodiment of this application provides an electronic device. The electronic device has a function of implementing behavior of an electronic device in the foregoing method for controlling a display of an electronic device. The function may be implemented by hardware, or may be implemented by hardware by executing corresponding software. The hardware or software includes one or more modules corresponding to the function.

DETAILED DESCRIPTION OF ILLUSTRATIVE EMBODIMENTS

Illustrative embodiments of this application include but are not limited to an authentication method, a medium, and an electronic device.

The following describes technical solutions in embodiments of this application with reference to accompanying drawings in embodiments of this application. In descriptions of embodiments of this application, unless otherwise specified, "/" means "or". For example, A/B may represent A or B. In this specification, "and/or" describes only an association relationship for describing associated objects and represents that three relationships may exist. For example, A and/or B may represent the following three cases: Only A exists, both A and B exist, and only B exists. In addition, in the descriptions in embodiments of this application, "a plurality of" means two or more.

Embodiments described in this specification may relate to operations and features of a wearable electronic apparatus. The wearable electronic apparatus may be configured to detect, in a measurement or another manner, a motion experienced by the wearable electronic apparatus. For ease of discussion, refer to description of a display of the wearable electronic apparatus. A display is usually located on user's wrist. Although embodiments may be described with reference to the fact that the display of the wearable electronic apparatus is usually located on user's wrist, the scope of the present invention is not limited thereto. The wearable electronic apparatus may be modified, so that the wearable electronic apparatus can be worn at different locations of the body (for example, a higher location on a forearm, an opposite side of the forearm, a leg, and a trunk). This will be understood by a person of ordinary skill in the art.

The following further describes in detail embodiments of this application with reference to the accompanying drawings.

Figure 1A:
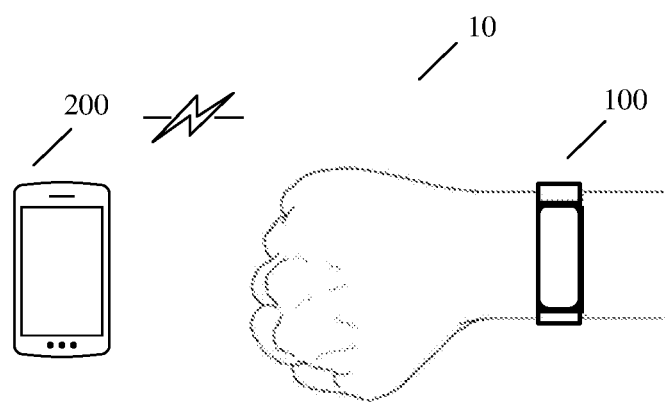
FIG. 1a is a diagram of an application scenario of a wearable electronic device according to some embodiments of this application.

FIG. 1a shows a detection system 10 in which the technical solutions in this application are used to control an electronic device to perform PPG detection. Specifically, as shown in FIG. 1a, the detection system 10 includes an electronic device 100 and an electronic device 200. The electronic device 100 includes a PPG sensor, and can analyze historical detection data of the electronic device 100 in a process of performing PPG detection on a user, to dynamically adjust light sources and photoelectric sensing elements that need to be turned on by the PPG sensor in different time segments. It may be understood that the electronic device 100 may be various electronic devices that can perform PPG detection on the user, for example, a wearable electronic device such as a band, a smartwatch, glasses, a helmet, and a headband, and a medical detection instrument. The following uses the band 100 shown in FIG. 1a as an example for description.

The electronic device 200 may be a client that can communicate with the electronic device 100, to help the electronic device 100 complete registration, control firmware update of the electronic device 100, receive test data of the electronic device 100, and assist the electronic device 100 in analyzing historical detection data to dynamically determine a light source and a photoelectric sensing element that are to be turned on by the PPG sensor in a use process. It may be understood that the electronic device 200 may include but is not limited to a laptop computer, a desktop computer, a tablet computer, a smartphone, a wearable device, a head-mounted display, a mobile email device, a portable game console, a portable music player, a reader device, a television set in which one or more processors are embedded or coupled, or another electronic device that can access a network. The following uses the mobile phone 200 shown in FIG. 1a as an example for description.

Figure 1B:
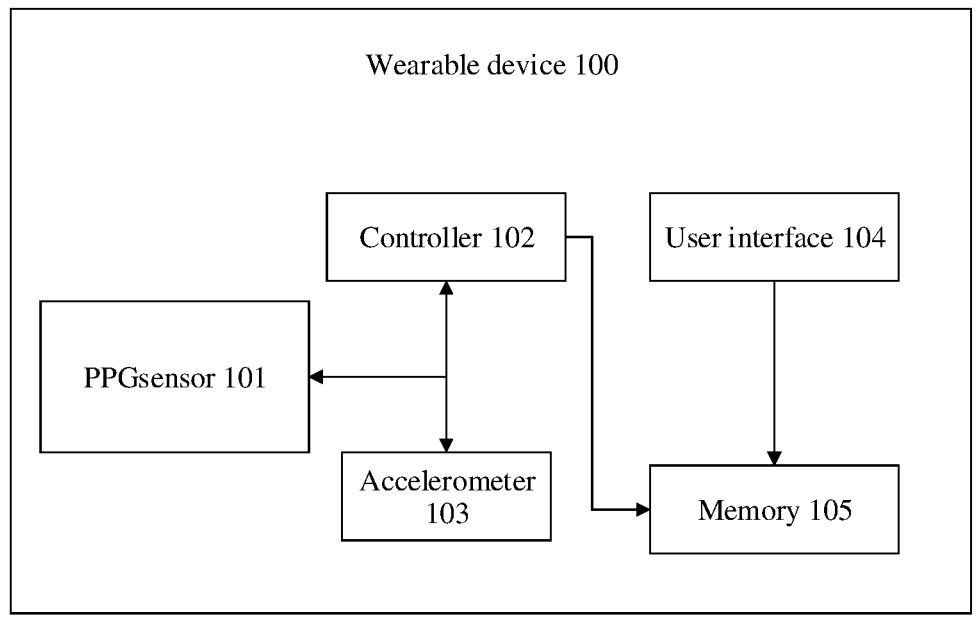
FIG. 1b is a diagram of a structure of a wearable electronic device according to some embodiments of this application.

FIG. 1b is a schematic diagram of a structure of the band 100 according to an embodiment of this application. Specifically, as shown in FIG. 1b, the band 100 may include a photoplethysmography (PPG) sensor 101, a controller 102, an accelerometer 103, a user interface 104, and a memory 105. The controller 102 is connected to both the memory 105 and the PPG sensor 101.

Figure 1C:
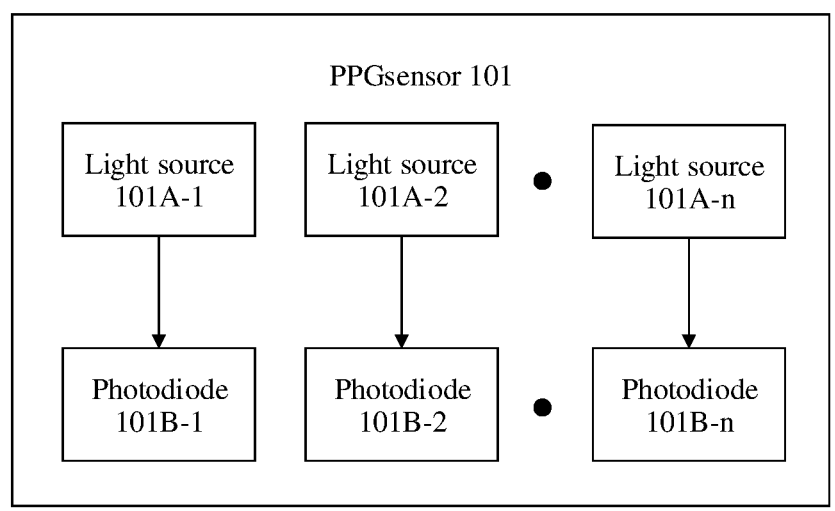
FIG. 1c is a schematic diagram of a structure of a PPG sensor according to some embodiments of this application.

The PPG sensor 101 may include a plurality of light sources and photoelectric sensing elements corresponding to the light sources, to implement PPG detection. FIG. 1c is a schematic diagram of a structure of the PPG sensor 101 according to an embodiment of this application. Specifically, as shown in FIG. 1c, the PPG sensor 101 may include a light source 101A-1 to a light source 101A-n and a photodiode 101B-1 to a photodiode 101B-n, where n is an integer greater than or equal to 2.

It may be understood that, although light sources are in a one-to-one correspondence with photodiodes in the embodiment shown in FIG. 1c, light sources may not be in a one-to-one correspondence with photodiodes in another embodiment. For example, there are n light sources, but there are m photodiodes, where m is an integer less than n. This is not limited in this application herein. The light source may be a green light source, a red light source, an infrared light source, or the like. For example, the light source may be a blue light emitting diode (Light Emitting Diode, LED). In addition, although the photoelectric sensing element shown in FIG. 1c in this application is a photodiode PD, it may be understood that the photoelectric sensing element may alternatively be another photoelectric sensing element herein.

The controller 102 is a control center of a collection system 100. The controller 102 may be one or more general-purpose central processing units, microprocessors, or the like, or may be an application-specific integrated circuit (ASIC), an electronic circuit, or the like. The controller 102 may further control a driver of each light source (LED) to control turn-on, turn-off, and the like of each light source. In addition, the controller 102 may also receive a signal from the PPG sensor 101 and the user interface 104, and send a signal to the PPG sensor 101 and the user interface 104.

The accelerometer 103 is configured to: receive a signal sent by the controller 102, and send a signal to the controller 102. The signal received by the accelerometer 103 may include original sensor data and/or sensor data obtained through filtering or processing. In embodiments of this application, the accelerometer 103 may be configured to: sense a motion status of the user, to learn whether the user is in a still state when the wearable electronic device is worn by the user, and obtain motion information of the user.

The user interface 104 is configured to exchange information between the system and the user, and may implement user registration and login. The user interface is usually a software interface, and may include a command interface, a program interface, and a graphic interface, that is, software developed based on a hardware device interface for human-machine connection.

The memory 105 may be configured to store instructions executed by the controller 102 and intermediate data generated during instruction execution, and may be configured to store detection data detected by the PPG sensor, the accelerometer, and the like. In addition, in some embodiments, the memory 105 may be further configured to store a correspondence between light source information of each light source and an identity of a detected user. The light source information may include light intensity and a light intensity sensing range of the light source, and different identities of detected users may be used to indicate different detected users.

A wireless communications module 1o6 may usually include one or more modules, and allows wireless communication between the mobile terminal 100 and a wireless communications system, communication between the mobile terminal 100 and another mobile terminal, communication between the mobile terminal 200 and an external server, and the like. In addition, in some embodiments, the memory 105 may further store personal information of a detected user that is used for the first time (for example, gender information, age information, whether the detected user smokes, whether the detected user drinks, and whether the detected user has heart disease, coronary heart disease, or hyperthyroidism), and atrial fibrillation load data, heart rate information, and motion information of the user in a historical record of the wearable electronic device (for example, the band 100).

The following describes in detail a specific process of controlling the PPG sensor shown in FIG. 1 to perform PPG measurement by using the technical solution of this application.

User Registration

When using the band 100 for the first time, the user needs to first perform user registration. For example, the user interface 104 performs user registration.

Specifically, in some embodiments, if there is a component that interacts with the user in the band 100, the user may perform registration by using the band 100. Specifically, for example, when the user performs user registration by using the band 100, the band may collect personal information of the user (for example, gender information, age information, whether the user smokes, whether the user drinks, motion information, a medical history such as heart disease or coronary heart disease) through the user interface 104, and store the information in the memory 105.

In some other embodiments, the user may register with the band 100 by using the mobile phone 200. For example, the mobile phone 200 may prompt, by using a screen of the mobile phone 200, the user to enter personal information of the user, and store the personal information of the user in a memory of the mobile phone 200 or send the personal information of the user to the band 100.

In addition, in some embodiments, a time for performing update by the band 100 (for example, 6:00 a.m. every day) may be set. When performing update, the band 100 may synchronize data with the mobile phone 100. For example, the band 100 sends detection data to the mobile phone 200, or obtains other related information from the mobile phone 200, for example, updated user information and motion information of the user (it is assumed that the mobile phone can detect motion of the user).

Initialization of the PPG Sensor

When using the band 100 for the first time, the user needs to initialize the PPG sensor 101, to determine a light source (namely, an initial light source) and a photodiode (namely, an initial photoelectric sensing element) of the PPG sensor 101 that are to be turned on in an initial condition.

In addition, in some embodiments, the band 100 is provided with a day mode and a night mode. When switching between the two modes is performed, the PPG sensor 101 needs to be initialized. This is because activity frequencies of the user are different in different time segments during the day and the night. During the day (for example, 6:00 to 18:00), the activity frequency of the user is relatively high, and the PPG sensor 101 needs to turn on a relatively large quantity of light sources when performing PPG measurement. However, during the night (for example, 18:00 to 6:00), the activity frequency of the user is relatively low, and the PPG sensor 101 may turn on a smaller quantity of light sources than that during the day when performing PPG measurement.

In addition, in some embodiments, as described above, the band 100 may be set to update data everyday (for example, at 6:00 a.m. every day). After performing update, and synchronizing data with the mobile phone 100, the band 100 may also initialize the PPG sensor 101.

The process of initializing the PPG sensor 101 and determining an initial light source and an initial PD that are to be turned on in an initial condition may be implemented by the mobile phone 200, or may be implemented by the band 100.

The following describes in detail several methods for initializing the PPG sensor 101.

(1) Initialize the PPG sensor based on a health risk of the user.

In this application, the health risk of the user may be calculated by using various probability output models based on regular information of the user (for example, user information, motion information, and a current measurement time). For example, in some embodiments, the health risk may be calculated by using a logistic regression model. Specifically, the health risk is calculated by using the following formula (1):

$$r=1/(1+e^{\wedge}(-\theta Tx)) \qquad (1).$$

Herein, r represents a health risk, and a higher value of r indicates a higher health risk of the user; the vector x represents a health risk parameter, for example, gender information, age information, whether the user smokes, whether the user drinks, and whether the user has heart disease, coronary heart disease, or hyperthyroidism; θ is a matrix, represents a weight of impact of the health risk parameter on health, and is obtained by previously training a large amount of data; and e is the base of the natural logarithm.

More specifically, for example, assuming that a user A smokes, does not drink, and has heart disease, x may be represented as (1, 0, 1)T, and θ is obtained through previous big data analysis, for example, (0.2, 0.2, 0.6)T, and represents a corresponding weight obtained through big data analysis. The health risk r of 0.69 may be calculated through substitution into the formula.

When a quantity of initial light sources of the PPG sensor is set, a higher risk r indicates a larger quantity of initial light sources, and an initial photodiode is an initial photodiode corresponding to an initial light source to be turned on.

In some embodiments, after the health risk r is obtained by using the foregoing regression model, a quantity of light sources to be turned on may be further calculated by using the following formula (2):

$$b=\text{Ceil}(r \times n) \qquad (2).$$

Herein, Ceil( ) is a ceiling function, b represents the calculated quantity of light sources to be turned on, and n is a maximum quantity of light sources supported by the PPG sensor 101.

Assuming that four light sources are disposed on the PPG sensor of the band 100 in total, n is equal to 4 herein. If b calculated by using the foregoing formula is equal to 3, it indicates that three light sources are turned on in an initialization condition, and any three of the four light sources may be selected as initial light sources.

(2) Initialize the PPG sensor 101 based on a health risk of the user and a time mode of the band 100 (a day mode and a night mode).

In this application, the PPG sensor 101 may alternatively be initialized based on both the health risk and the current time mode of the band 100.

For example, it is assumed that the band 100 has four light sources and four PDs in total, and b calculated according to the foregoing formula (1) and formula (2) is equal to 3. If a current measurement time is in a measurement time segment of the day mode, four light sources are turned on as initial light sources. If a current measurement time is in a measurement time segment of the night mode, three or two light sources are turned on as initial light sources.

That is, when the PPG sensor 101 is initialized based on the health risk and the time mode of the band 100, a quantity of light sources that need to be turned on and that are obtained based on the health risk may be appropriately increased in the day mode, and a quantity of light sources that need to be turned on and that are obtained based on the health risk may be appropriately decreased in the night mode.

Dynamic Adjustment of the PPG Sensor

Figure 2:
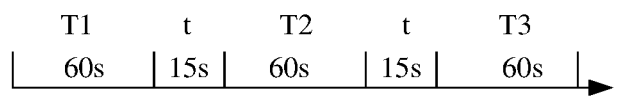
FIG. 2 is a schematic diagram of different detection time segments according to some embodiments of this application, where T1, T2, and T3 separately represent different detection time segments, and t represents duration of an interval between detection time segments.

When collecting PPG data, the band 100 performs periodic detection based on a specified periodicity, to periodically collect the PPG data. For example, as shown in FIG. 2, PPG data is collected once for one minute every 15 seconds. In addition, before the PPG data is collected, a current motion status of the user needs to be sensed by using the accelerometer 103, to further determine whether the user correctly wears the band, and determine signal quality by determining whether the user is in a still state. Specifically, if the user incorrectly wears the band or the user is not in a still state, a next collection moment is waited. If the user correctly wears the PPG and the user is in a still state, PPG data of a current light source is collected for one minute.

The following describes dynamic adjustment of the PPG sensor by using a feature related to atrial fibrillation detection. A confidence of an atrial fibrillation screening result is calculated by using the band 100.

In some embodiments, a quantity of light sources to be turned on is determined by using the confidence of the atrial fibrillation screening result. It may be understood that, in another embodiment, a quantity of light sources to be turned on may alternatively be determined by using another confidence, for example, pressure load or sleep quality.

The following describes a dynamic adjustment solution of the PPG sensor.

It is assumed that the PPG sensor has four light sources: 101A-1, 101A-2, 101A-3 and 101A-4.

Light source data in a previous measurement time segment is obtained. Specifically, as shown in FIG. 2, light source data Sa in a time segment T1 of 60 is obtained. T1, T2, and T3 separately represent different measurement time segments for collecting light source data, duration of each measurement time segment is 60 s, and t represents a time interval between different measurement time segments, where t=15 s.

A light source data confidence Ca of a current light source is calculated based on the light source data Sa.

Herein, all common models that can output a probability may usually be used as a confidence determining model. In this application, a logistic regression model is used as an example for description.

$$p=1/(1+e^{\wedge}(-\alpha^{\wedge}Tf)) \qquad (3).$$

$$c=2 \times \text{abs}(0.5-p) \qquad (4).$$

Herein, c is a confidence calculation result, and f is a feature related to atrial fibrillation detection, for example, heart rate variability.

α is a weight matrix corresponding to the feature related to atrial fibrillation detection, and is obtained through previous big data statistics training; e is the base of the natural logarithm; and p represents a possibility that the data is atrial fibrillation. More specifically, if p(PPG) is close to 0 or 1, the PPG record is close to non-atrial fibrillation or atrial fibrillation, and C(PPG) is close to 100%, indicating a high confidence. Alternatively, if p(PPG) is close to 0.5, it cannot be determined whether the PPG record is atrial fibrillation or non-atrial fibrillation, and C(PPG) is close to 0, indicating a low confidence. For example, it is assumed that f represents a heart rate variability feature, for example, a normalized standard difference and a mean with values of (0.5, 0.9). A value of a is obtained through previous big data analysis, for example, (0.6, 0.2)T. The probability of 0.62 that the data is determined as atrial fibrillation, and the confidence calculation result of 0.24 may be obtained through substitution into the formula, indicating a low confidence.

Then, it is determined, based on the light source data confidence Ca of the current light source, whether another light source different from the current light source is to be turned on.

In conclusion, in addition to the light source data confidence, a light source to be turned on in a next detection time segment may be further determined with reference to other information.

In embodiments of this application, a confidence threshold is set to 95%. Specifically, a process of determining, based on the light source data confidence Ca of the current light source data, whether another light source different from the current light source is to be turned on may be determined by the mobile phone 200 by controlling the band 100, or may be determined by the band 100. A specific determining method may be any one of the following methods.

Figure 3A:
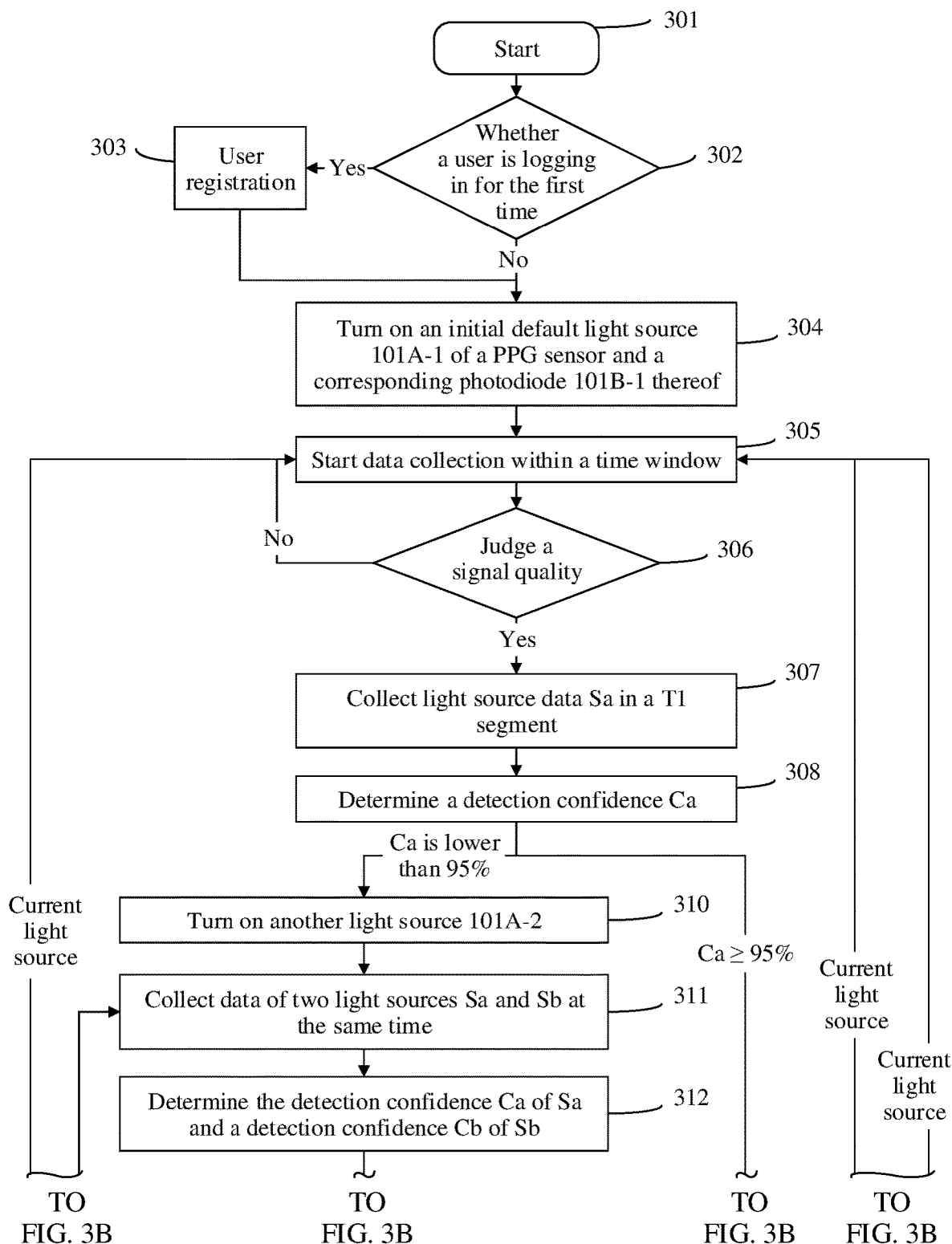
FIG. 3A to FIG. 3C are a flowchart of an electronic device and a method for controlling an electronic device to perform PPG detection according to some embodiments of this application.
Figure 3B:
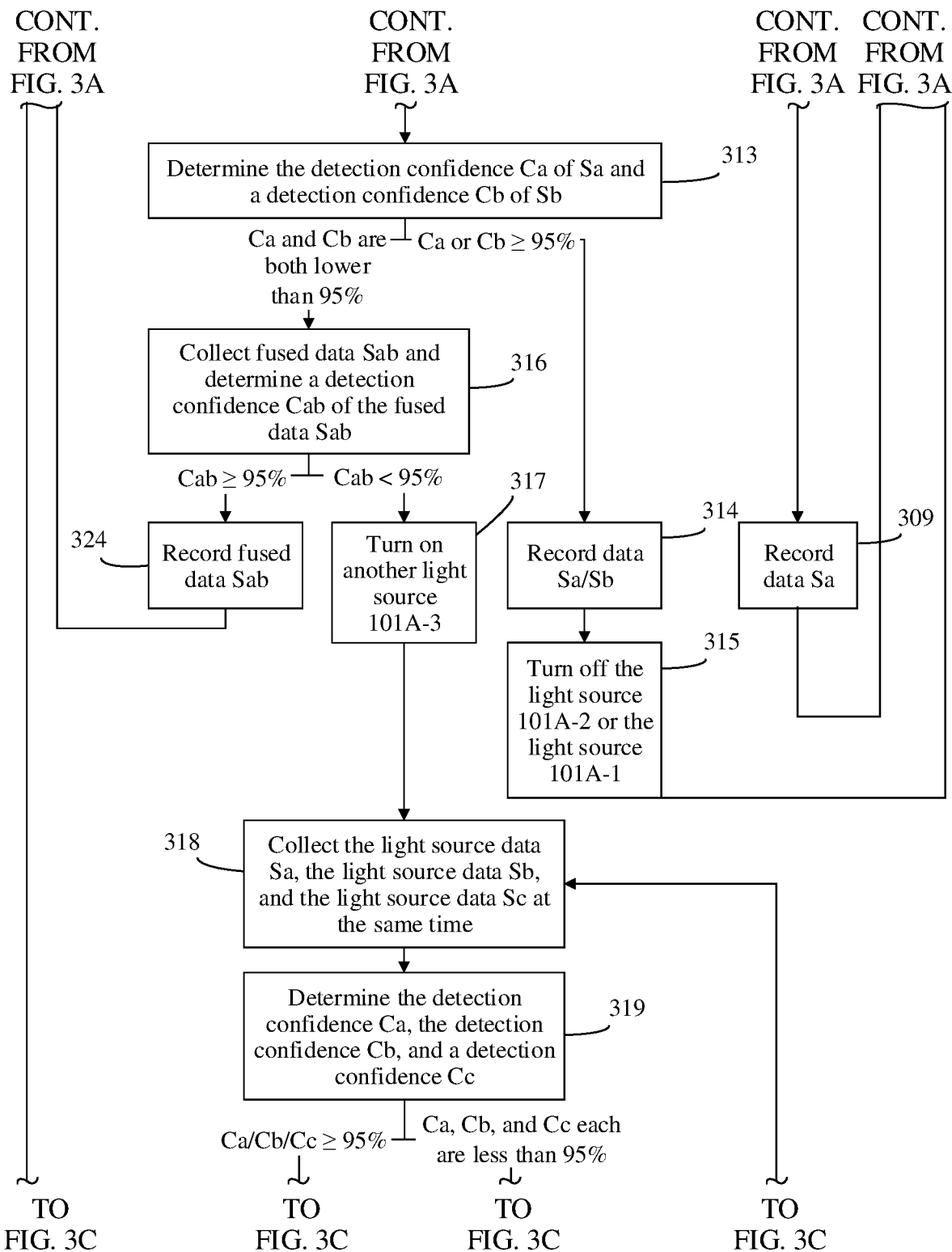
Figure 3C:
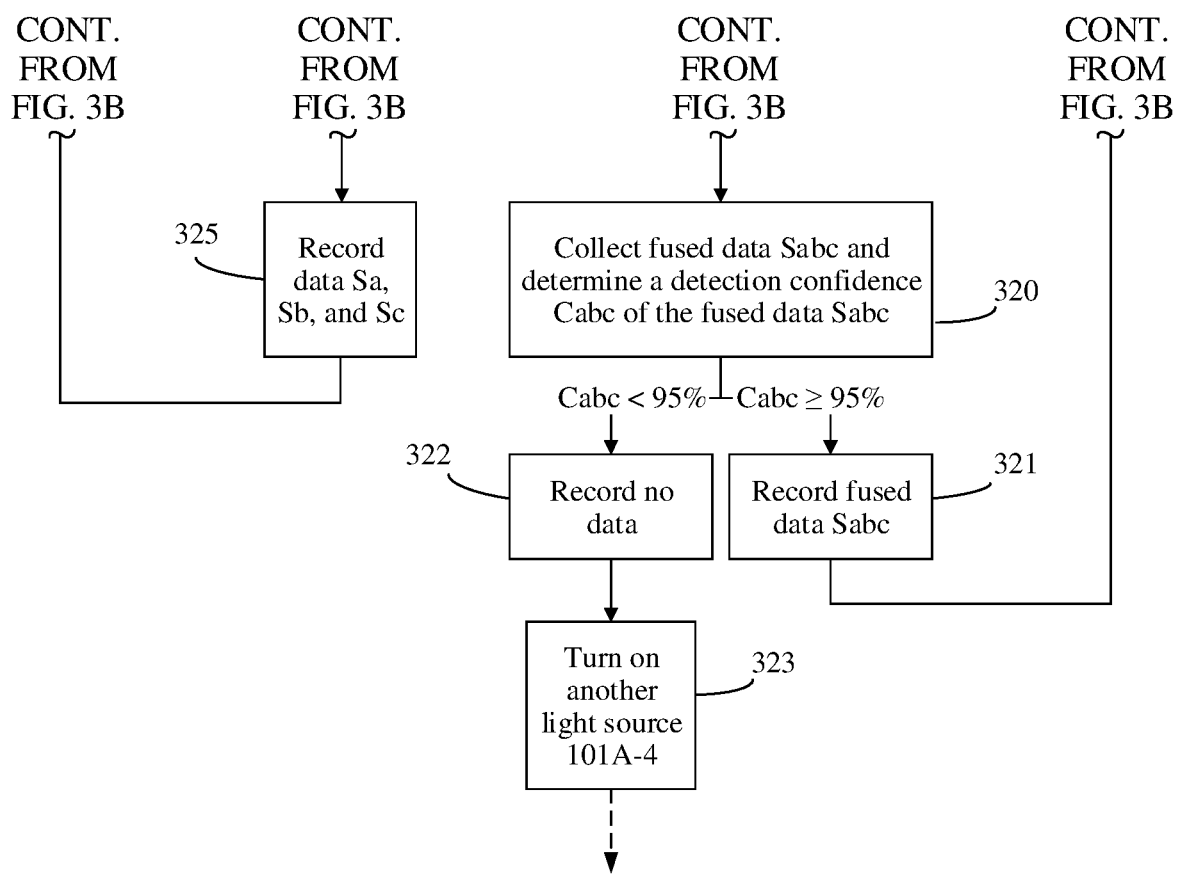

As shown in FIG. 3A to FIG. 3C, it is first determined whether a user performs login for the first time (302). If the user performs login for the first time, user registration is first performed (303).

If the user does not perform login for the first time, an initial default PPG sensor light source 101A-1 and a photodiode 101B-1 corresponding to the PPG sensor light source 101A-1 are turned on (304). In embodiments, light sources are in a one-to-one correspondence with photodiodes. When a light source is turned on, a photodiode corresponding to the light source is turned on by default.

Data collection is started in a time window (305). Collected signal quality is determined by using motion information of the user, that is, whether the user is in a still state and whether the user correctly wears the band (306). If the user does not correctly wear the band or is in a motion state, data collection is restarted in a time window (305). If the user is in a still state and correctly wears the band, light source data Sa in a time segment T1 is collected (307).

A confidence Ca of Sa is calculated by using the foregoing confidence calculation method, and the detection confidence Ca is determined (308).

When Ca is greater than or equal to 95%, the light source data Sa of the light source 101A-1 is recorded, and the light source data of the light source 101A-1 is still collected in a next detection time segment T2 (309).

When Ca is less than 95%, another light source 101A-2 and a photodiode 101B-2 corresponding to the light source 101A-2 are turned on (310). Two pieces of light source data Sa and Sb are simultaneously collected (311). Detection confidences Ca and Cb of Sa and Sb are determined (312). If Ca is greater than or equal to 95%, the light source data Sa is recorded (314). If Cb is greater than or equal to 95%, the light source data Sb is recorded (314). If both Ca and Cb are greater than or equal to 95%, either the light source 101A-1 or the light source 101A-2 is turned off (315). The light source 101A-2 or the light source 101A-1 is used in the next detection time segment T2 (315).

When both Ca and Cb are less than 95%, a confidence Cab of fused data Sab of the light source 101A-1 and the light source 101A-2 is determined (316). When Cab is greater than or equal to 95%, the data Sab is recorded (324). The two light sources 101A-1 and 101A-2 are simultaneously turned on in the next detection time segment T2.

When Cab is less than 95%, another light source 101A-3 is turned on (317). Three pieces of light source data Sa, Sb, and Sc of the three light sources are simultaneously collected (318). Detection confidences Ca, Cb, and Cc are determined (319). If any one of Ca, Cb, and Cc is greater than 95%, the light source data Sa, Sb, or Sc is recorded (325). If Ca, Cb, and Cc are all greater than or equal to 95%, light source data with a highest confidence is recorded, and the light source with the highest confidence in the light sources 101A-1, 101A-2, and 101A-3 is used in the next detection time segment T2.

When Ca, Cb, and Cc are all less than 95%, fused data Sabc is collected and a detection confidence Cabc is determined (320). When Cabc is greater than or equal to 95%, the data Sabc is recorded (321). Three light sources are turned on in the next detection time segment T2, and the fused data Sabc is collected.

When Cabc is less than 95%, no data is recorded (322). A fourth light source 101A-4 is turned on.

Figure 4A:
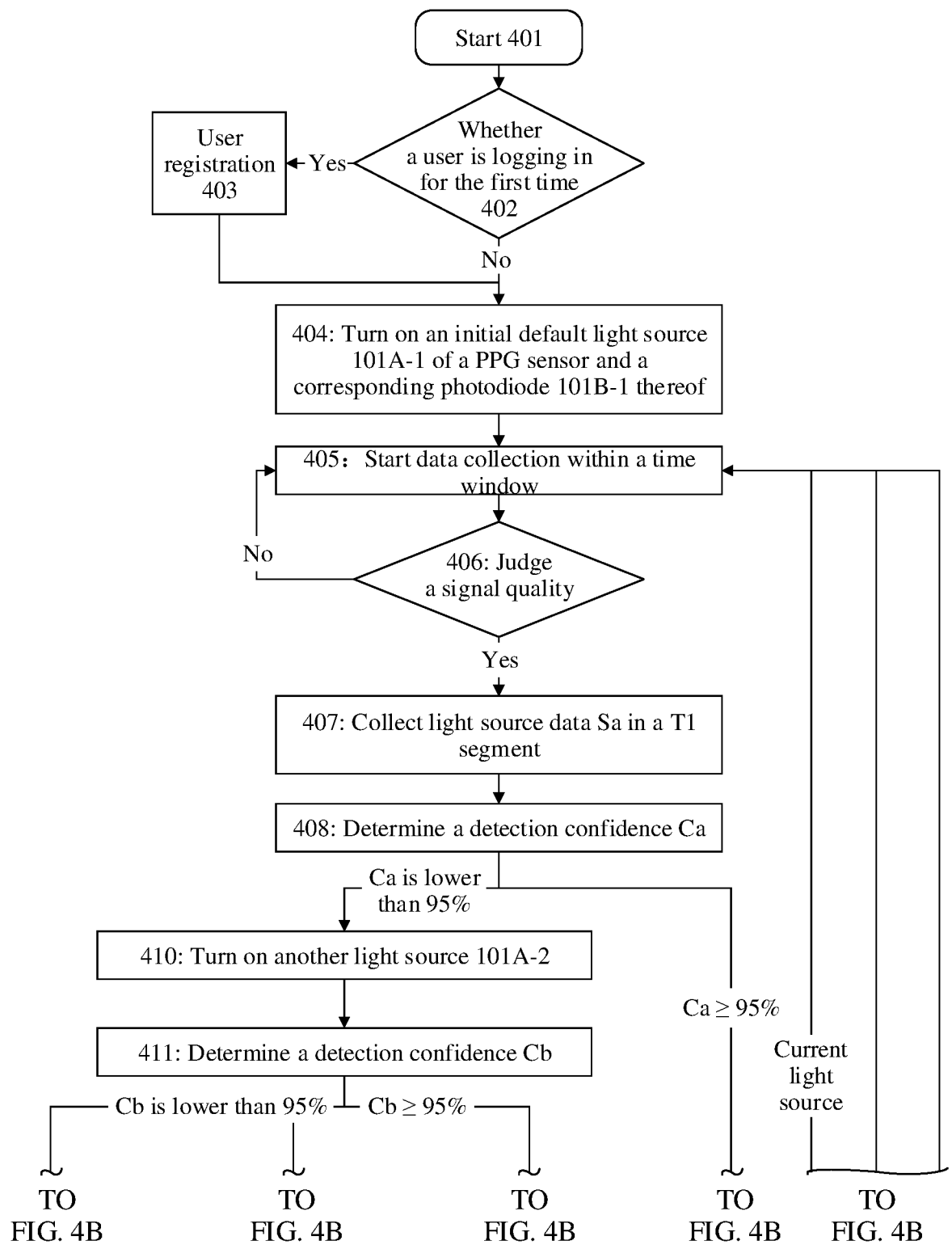
FIG. 4A to FIG. 4C are a flowchart of an electronic device and a method for controlling an electronic device to perform PPG detection according to some embodiments of this application.
Figure 4B:
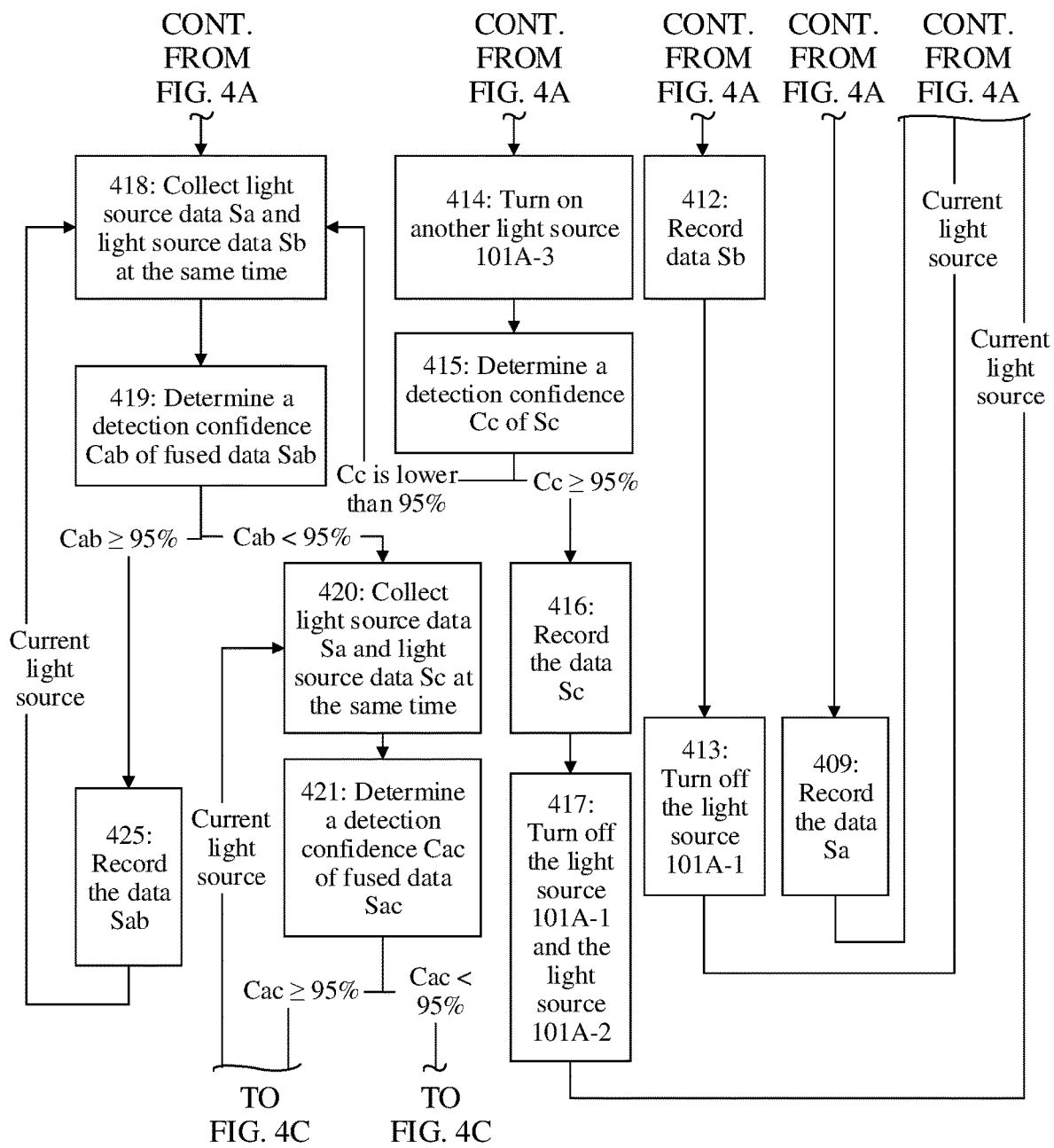
Figure 4C:
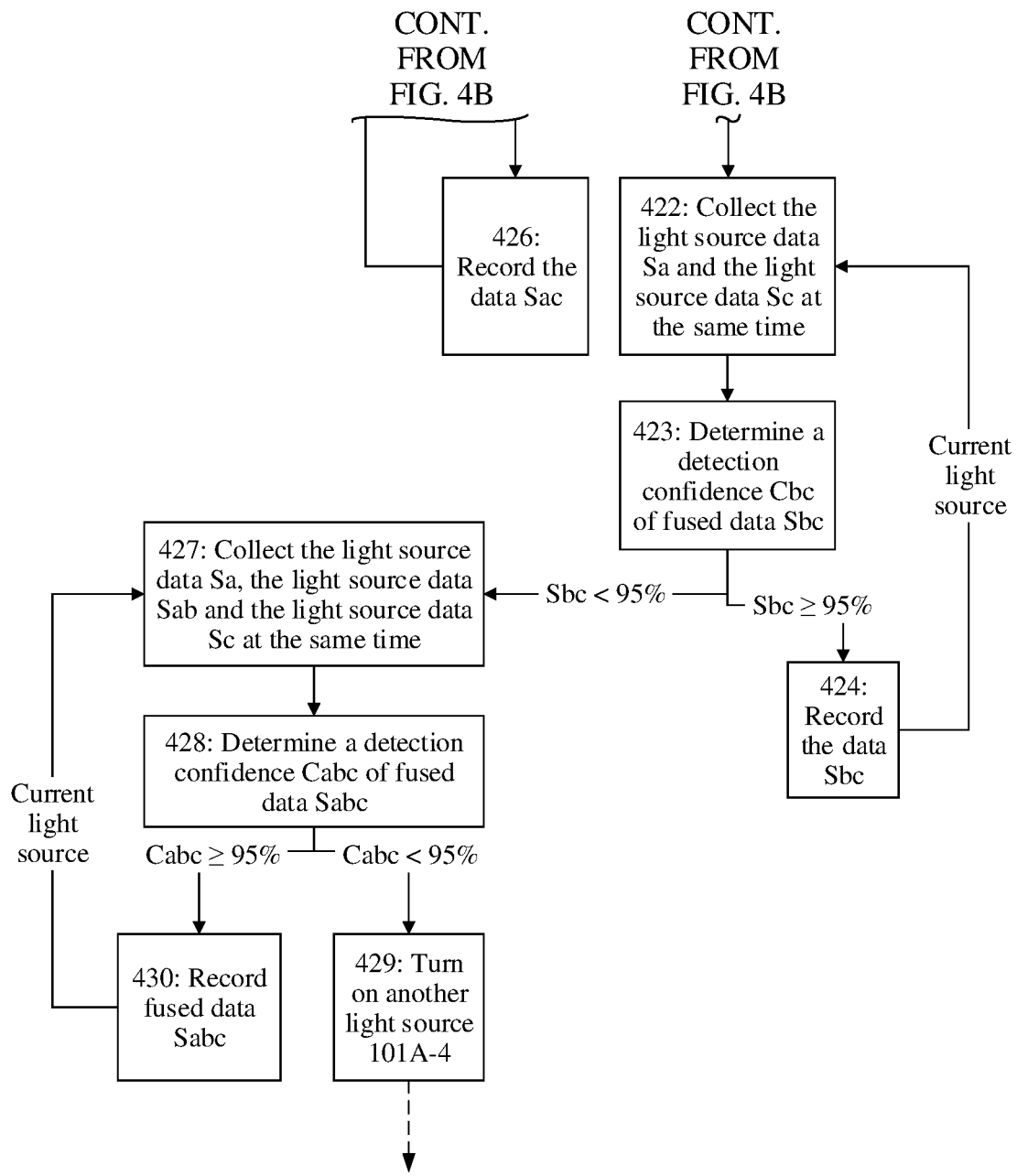

Optionally, as shown in FIG. 4A to FIG. 4C, the foregoing determining process may alternatively be as follows:

When Ca is greater than or equal to 95%, light source data Sa of the light source 101A-1 is recorded, and the light source data of the light source 101A-1 is still collected in a next detection time segment T2.

When Ca is less than 95%, another light source 101A-2 is turned on, light source data Sb is collected, and Cb is determined. When Cb is greater than or equal to 95%, the light source data Sb is recorded, and the light source data of the light source 101A-2 is collected in the next detection time segment T2.

It is assumed that Cb is less than 95%.

(1) Another light source 101A-3 is turned on, light source data Sc is collected, and Cc is determined. When Cc is greater than or equal to 95%, the light source data Sc is recorded, and light source data of the light source 101A-3 is collected in the next detection time segment T2.

When Cc is less than 95%, fused data Sab of the light sources 101A-1 and 101A-2 is collected, and Cab is determined. When Cab is greater than or equal to 95%, the light source data Sab is recorded, and the light sources 101A-1 and 101A-2 are simultaneously turned on, and the fused data Sab is collected in the next detection time segment T2.

(2) Alternatively, fused data Sab of the light sources 101A-1 and 101A-2 is collected, and Cab is determined. When Cab is greater than or equal to 95%, the light source data Sab is recorded, and the light sources 101A-1 and 101A-2 are simultaneously turned on, and the fused data Sab is collected in the next detection time segment T2.

It is assumed that Cab is less than 95%.

(1) Light source data Sac is collected, and Cab is determined. If Cac is greater than or equal to 95%, the data Sac is recorded, and the light sources 101A-1 and 101A-3 are simultaneously turned on in the next detection time segment T2.

When Cac is less than 95%, Sabc is collected, and Cabc is determined. If Cabc is greater than or equal to 95%, the fused data Cabc is recorded, and the three light sources are simultaneously turned on in the next detection time segment T2.

(2) Alternatively, light source data Sabc is directly collected, and Cabc is determined. If Cabc is greater than or equal to 95%, the fused data Cabc is recorded, and the three light sources are simultaneously turned on in the next detection time segment T2.

If Cabc is less than 95%, no data is recorded, and a fourth light source 11A-4 is turned on in the next detection time segment T2.

Figure 5A:
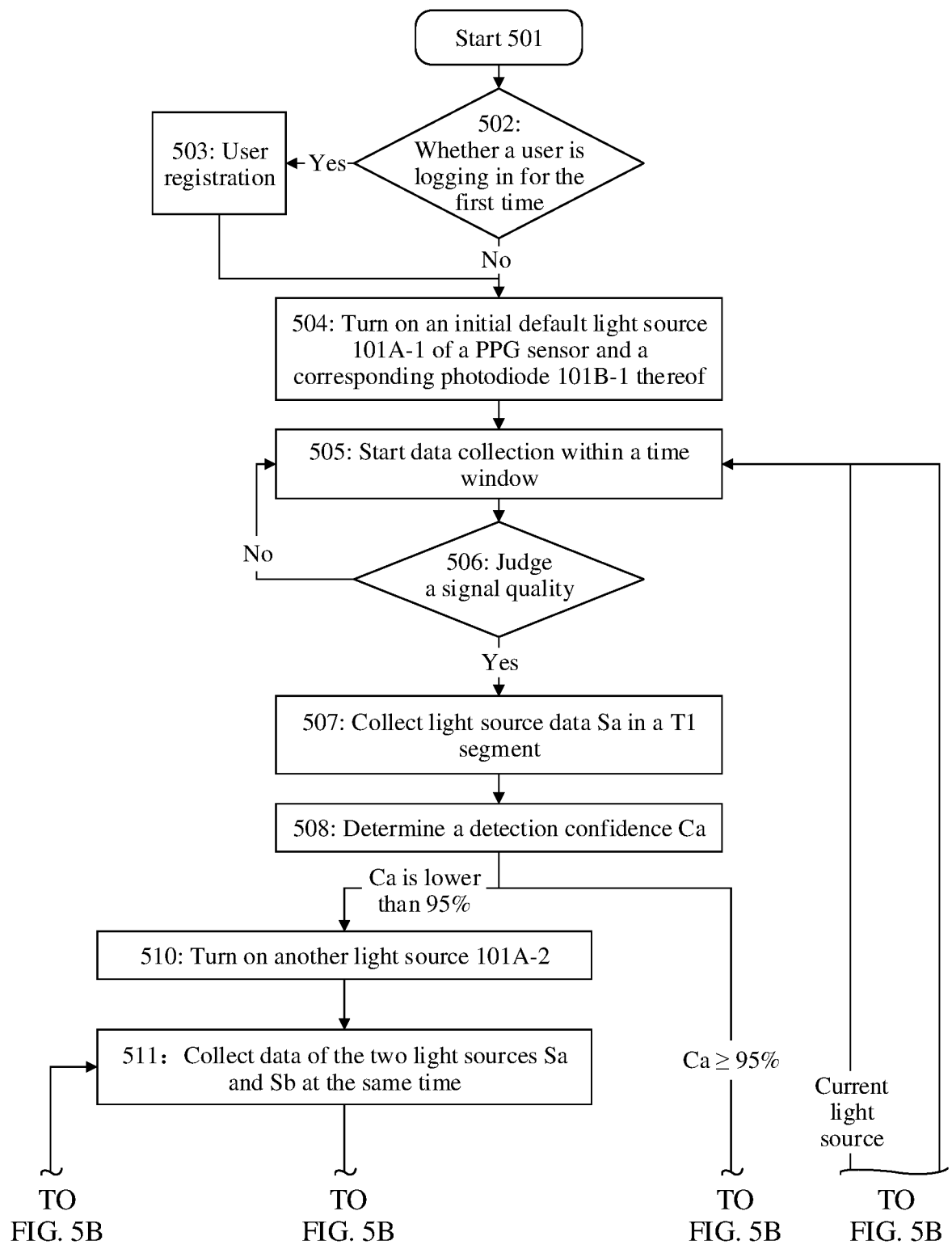
FIG. 5A and FIG. 5B are a flowchart of an electronic device and a method for controlling an electronic device to perform PPG detection according to some embodiments of this application.
Figure 5B:
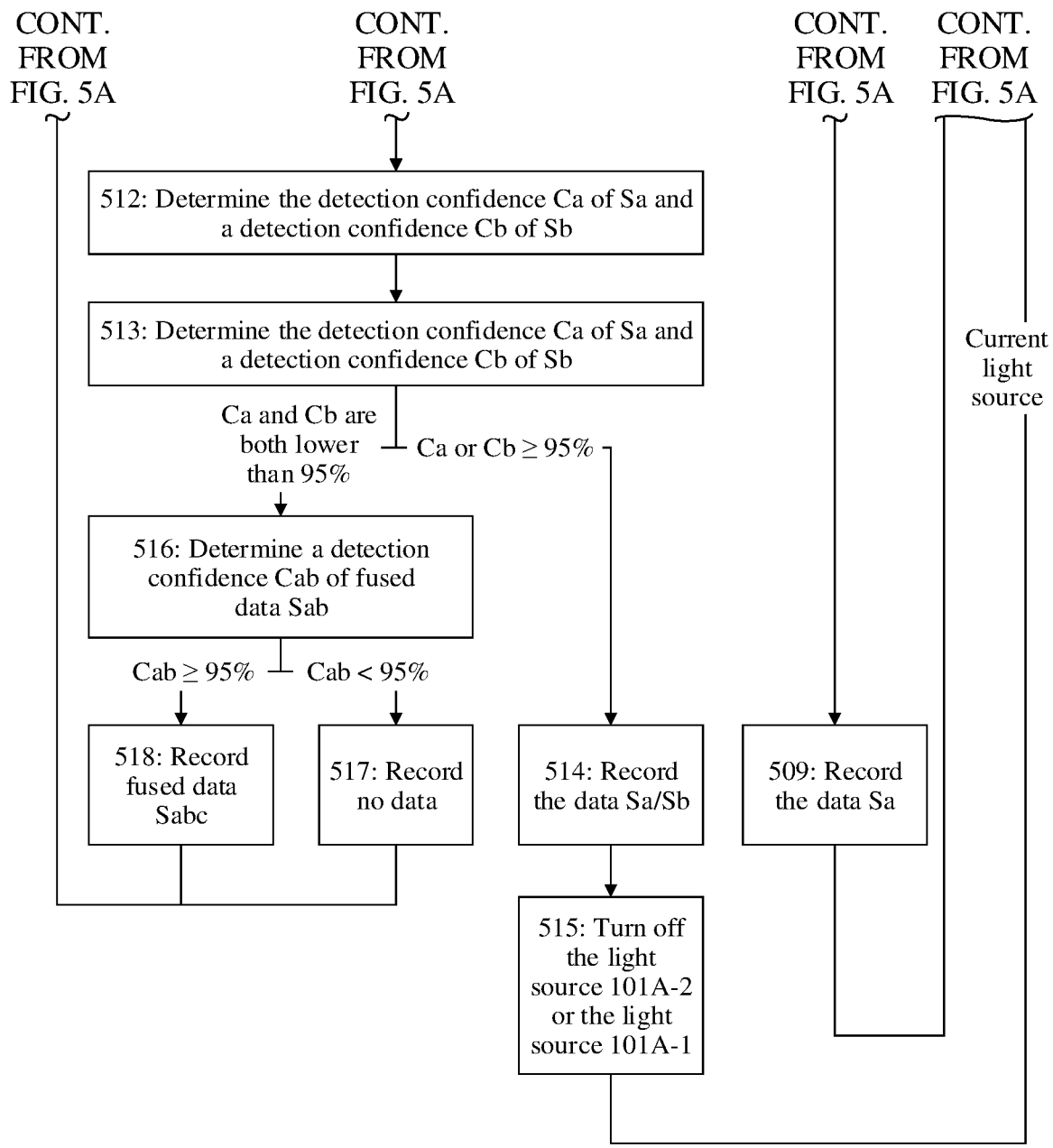

In another embodiment of this application, there may be two light sources: 101A-1 and 11A-2. The foregoing related calculation method and determining method are still applicable to embodiments. To avoid complexity, details are not described herein again. As shown in FIG. 5A and FIG. 5B, a procedure of the method is as follows:

If a default initial light source is 101A-1, light source data Sa in a time segment T1 is collected, and a confidence Ca of the light source data is detected.

When Ca is greater than or equal to 95%, the light source data Sa of the light source 101A-1 is recorded, and the light source data of the light source 101A-1 is still collected in a next detection time segment T2.

When Ca is less than 95%, another light source 101A-2 is turned on. Two pieces of light source data Sa and Sb are simultaneously collected. Detection confidences Ca and Cb of Sa and Sb are determined. If Ca is greater than or equal to 95%, the light source data Sa is recorded. If Cb is greater than or equal to 95%, the light source data Sb is recorded. If both Ca and Cb are greater than or equal to 95%, the light source 101A-1 or 101A-2 with a lower confidence is turned off. The light source 101A-2 or the light source 101A-1 is used in the next detection time segment T2.

When both Ca and Cb are less than 95%, fused data Sab of the light source 101A-1 and the light source 101A-2 is collected, and a confidence Cab is determined. When Cab is greater than or equal to 95%, the data Cab is recorded. The two light sources 101A-1 and 101A-2 are simultaneously turned on in the next detection time segment T2. When Cab is less than 95%, no data is recorded, and the two light sources 101A-1 and 101A-2 are simultaneously turned on in the next detection time segment T2.

Figure 6A:
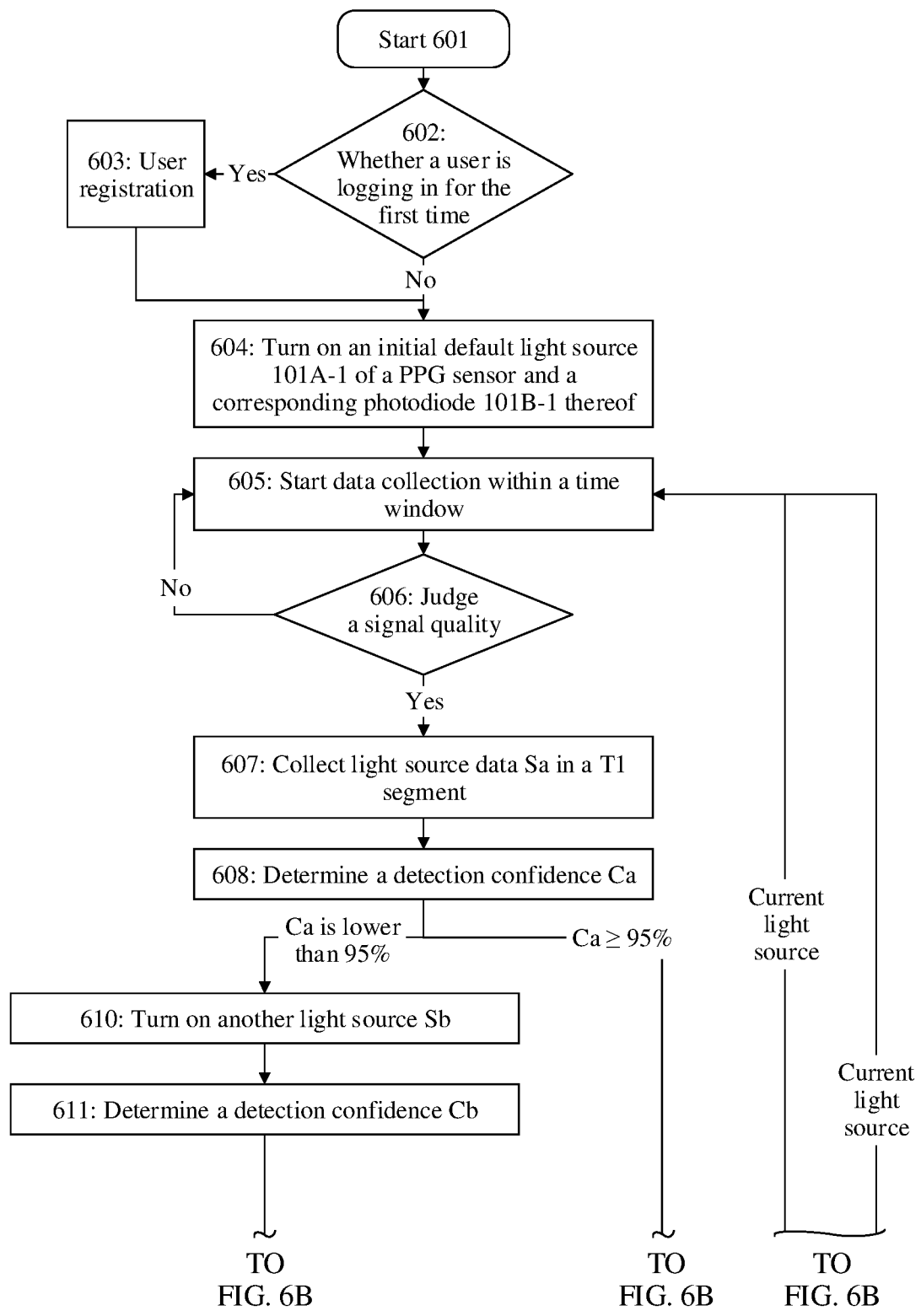
FIG. 6A and FIG. 6B are a flowchart of an electronic device and a method for controlling an electronic device to perform PPG detection according to some embodiments of this application.
Figure 6B:
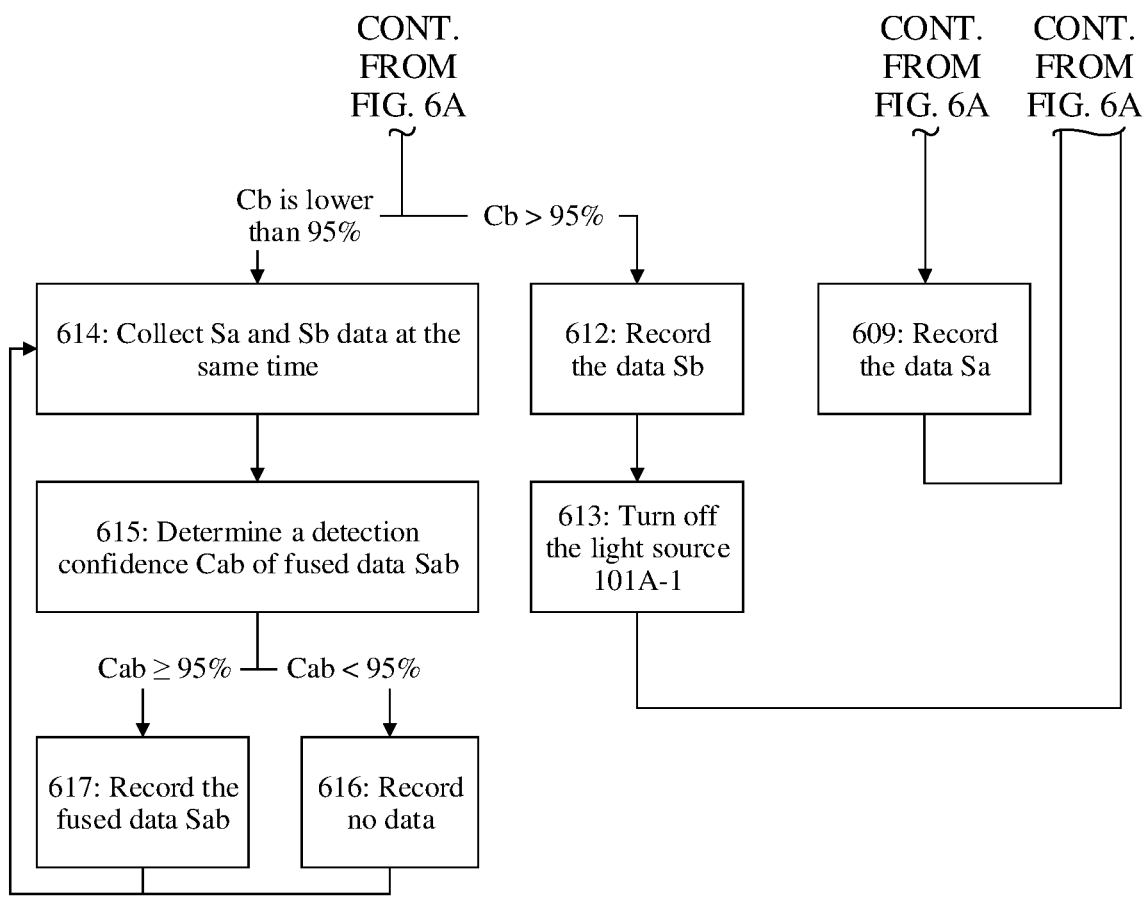

Optionally, as shown in FIG. 6A and FIG. 6B, the foregoing determining process may alternatively be as follows:

When Ca is greater than or equal to 95%, light source data Sa of the light source 101A-1 is recorded, and the light source data of the light source 101A-1 is still collected in a next detection time segment T2.

When Ca is less than 95%, another light source 101A-2 is turned on, light source data Sb is collected, and Cb is determined. When Cb is greater than or equal to 95%, the light source data Sb is recorded, and the light source data of the light source 101A-2 is collected in the next detection time segment T2.

When Cb is less than 95%, Sa and Sb are simultaneously collected, and a detection confidence Cab of fused data Sab is determined. When Cab is greater than or equal to 95%, the light source data Sab is recorded, and the light sources 101A-1 and 101A-2 are simultaneously turned on, and the fused data Sab is collected in the next detection time segment T2.

When Cab is less than 95%, the data Sab is not recorded, and the light sources 101A-1 and 101A-2 are simultaneously turned on, and the fused data Sab is collected in the next detection time segment T2.

It may be understood that a confidence of an atrial fibrillation screening result is used in embodiments of this application. In another specific embodiment, a confidence of a screening result may alternatively be obtained by using data information such as blood pressure information, pulse information, pressure load information, and sleep quality information. This is not limited in this application.

Figure 7:
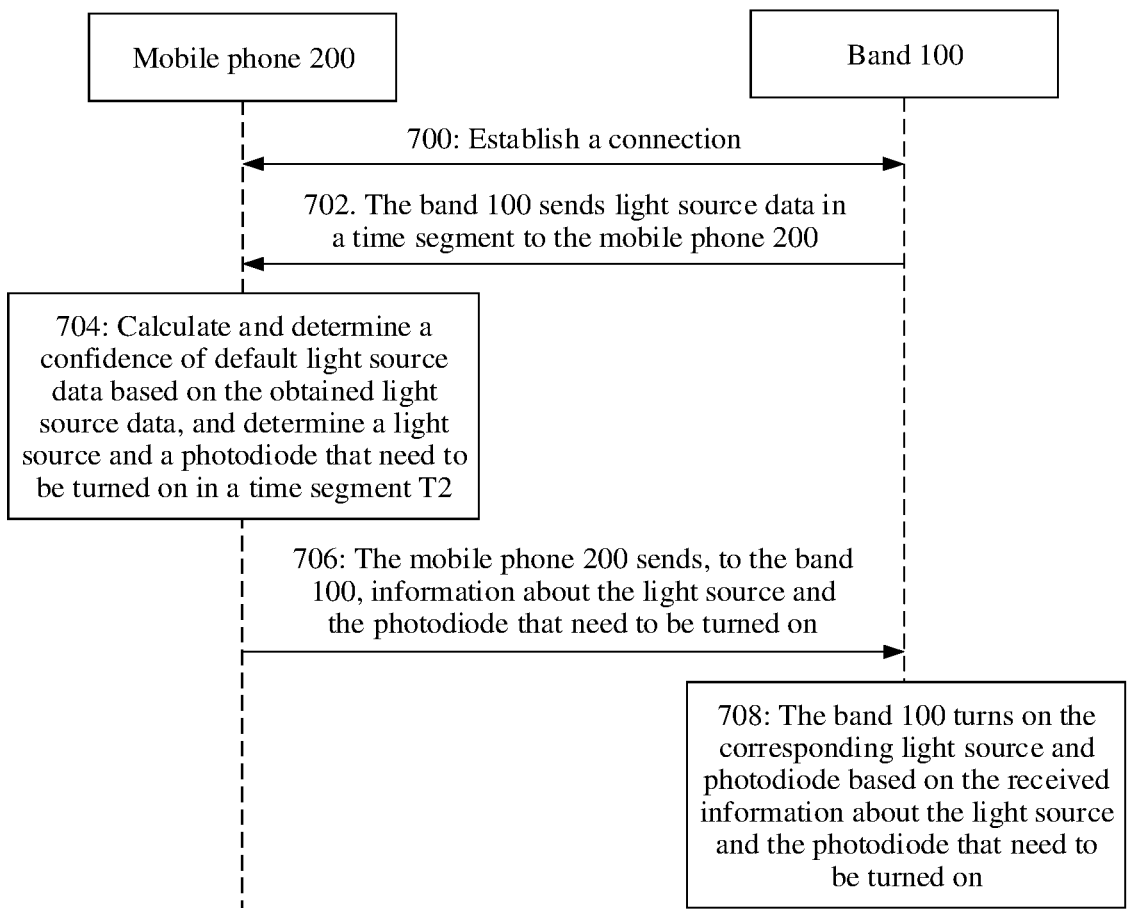
FIG. 7 is a schematic diagram of interaction between a band and a mobile phone according to some embodiments of this application.

It may be understood that, although the foregoing embodiment is described by using the confidence of the atrial fibrillation screening result calculated by the band 100, in another embodiment, the confidence of the atrial fibrillation screening result may alternatively be calculated by the mobile phone 200. For example, FIG. 7 is a schematic flowchart of calculating a confidence of an atrial fibrillation screening result by the mobile phone 200 according to an embodiment of this application. Details are shown in FIG. 7:

700: The mobile phone 200 establishes a communication connection to the band 100.

702: The mobile phone 200 obtains PPG data in a measurement time segment such as a time segment T1 from the band 100.

704: The mobile phone 200 calculates a confidence of an atrial fibrillation screening result of the PPG data based on the obtained PPG data in the time segment T1, and determines, based on the calculated confidence, a light source and a photodiode that need to be turned on in a time segment T2. A specific calculation manner and a policy of determining a light source and photodiode that are to be turned on are the same as those in the foregoing embodiment. Details are not described herein again.

706: The mobile phone 200 sends, to the band 100, information about the light source to be turned on and information about the photodiode to be turned on, for example, identifiers of the light source and the photodiode.

708: The band 100 turns on the light source and the photodiode based on the received information about the light source to be turned on and the received information about the photodiode to be turned on.

Figure 8:
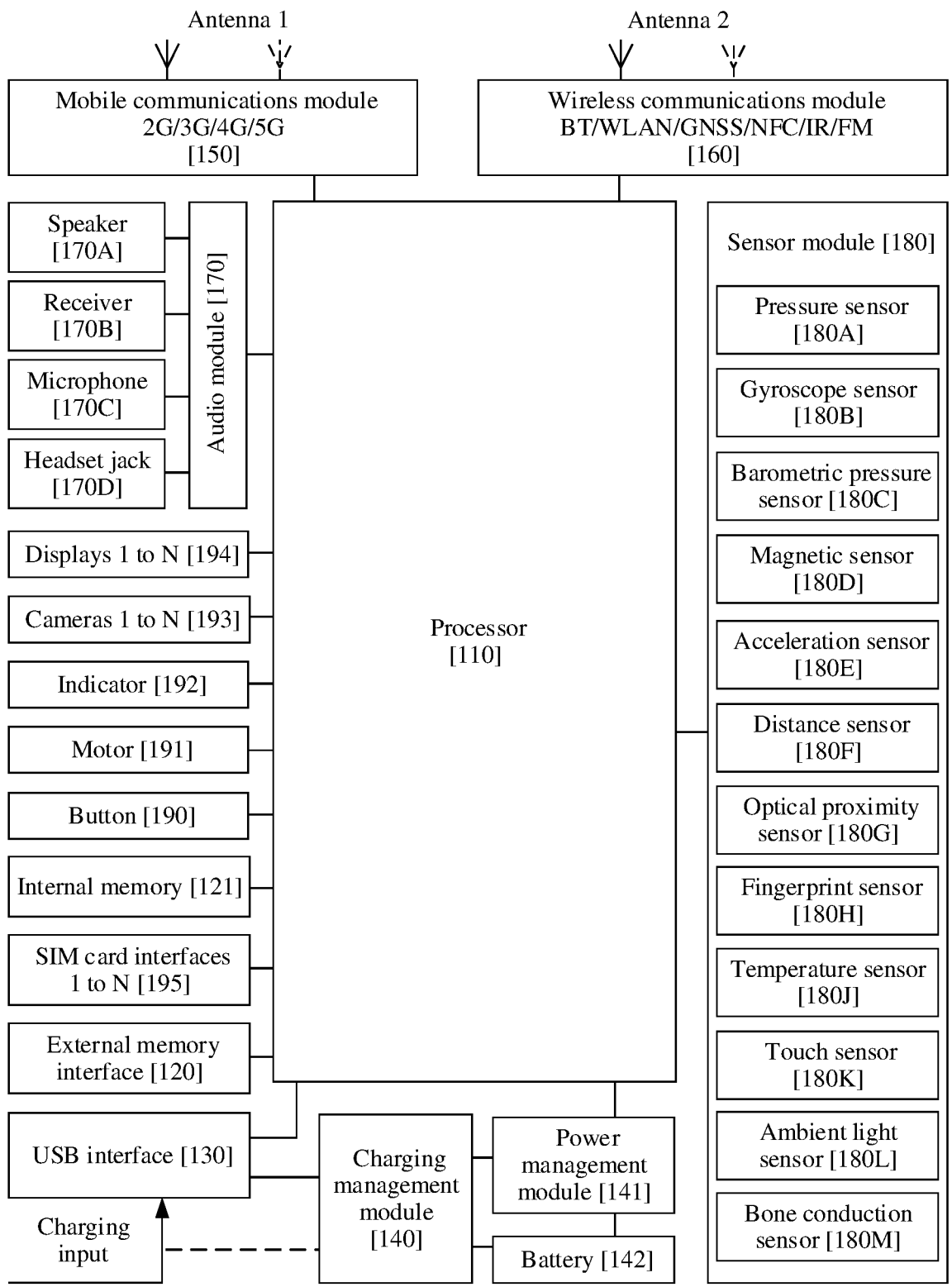
FIG. 8 is a schematic diagram of a structure of an electronic device according to some embodiments of this application.

FIG. 8 is a block diagram of a structure of an electronic device 800 that can implement a function of the electronic device 200 shown in FIG. 1 according to an embodiment of the present invention. Specifically, as shown in FIG. 8, the electronic device 800 may include a processor 110, an external memory interface 120, an internal memory 121, a universal serial bus (universal serial bus, USB) interface 130, a charging management module 140, a power management module 141, a battery 142, an antenna 1, an antenna 2, a mobile communications module 150, a wireless communications module 160, an audio module 170, a speaker 170A, a receiver 170B, a microphone 170C, a headset jack 170D, a sensor module 180, a button 190, a motor 191, an indicator 192, a camera 193, a display 194, a subscriber identification module (subscriber identification module, SIM) card interface 195, and the like. The sensor module 180 may include a pressure sensor 180A, a gyroscope sensor 180B, a barometric pressure sensor 180C, a magnetic sensor 180D, an acceleration sensor 180E, a distance sensor 180F, an optical proximity sensor 180G, a fingerprint sensor 180H, a temperature sensor 180J, a touch sensor 180K, an ambient light sensor 180L, a bone conduction sensor 180M, and the like.

It may be understood that the structure shown in this embodiment of the present invention does not constitute a specific limitation on the electronic device 800. In some other embodiments of this application, the electronic device 800 may include more or fewer components than those shown in the figure, or some components may be combined, or some components may be split, or different component arrangements may be used. The components shown in the figure may be implemented by hardware, software, or a combination of software and hardware.

The processor 110 may include one or more processing units. For example, the processor 110 may include an application processor (application processor, AP), a modem processor, a graphics processing unit (graphics processing unit, GPU), an image signal processor (image signal processor, ISP), a controller, a video codec, a digital signal processor (digital signal processor, DSP), a baseband processor, and/or a neural-network processing unit (neural-network processing unit, NPU). Different processing units may be independent devices, or may be integrated into one or more processors. For example, the electronic device may calculate a confidence of the atrial fibrillation screening result of the band 100.

The controller may generate an operation control signal based on an instruction operation code and a time sequence signal, to complete control of instruction reading and instruction execution.

A memory may be further disposed in the processor 110, and is configured to store instructions and data. In some embodiments, the memory in the processor 110 is a cache. The memory may store instructions or data that has been used or cyclically used by the processor 110. If the processor 110 needs to use the instructions or the data again, the processor 110 may directly invoke the instructions or the data from the memory. This avoids repeated access, reduces waiting time of the processor 110, and therefore improves system efficiency.

In some embodiments, the processor 110 may include one or more interfaces. The interface may include an inter-integrated circuit (inter-integrated circuit, I2C) interface, an inter-integrated circuit sound (inter-integrated circuit sound, I2S) interface, a pulse code modulation (pulse code modulation, PCM) interface, a universal asynchronous receiver/transmitter (universal asynchronous receiver/transmitter, UART) interface, a mobile industry processor interface (mobile industry processor interface, MIPI), a general-purpose input/output (general-purpose input/output, GPIO) interface, a subscriber identification module (subscriber identity module, SIM) interface, a universal serial bus (universal serial bus, USB) interface, and/or the like, and a micro USB port, a USB Type-C port, and the like. The USB port 130 may be configured to connect to a charger to charge the electronic device 800, or may be configured to perform data transmission between the electronic device 800 and a peripheral device, or may be configured to connect to a headset to play audio through the headset. Alternatively, the port may be configured to connect to another electronic device, for example, an AR device.

It may be understood that an interface connection relationship between the modules that is shown in this embodiment of the present invention is only an example for description, and constitutes no limitation on the structure of the electronic device 800. In some other embodiments of this application, the electronic device 800 may alternatively use an interface connection manner different from that in the foregoing embodiment, or a combination of a plurality of interface connection manners.

The charging management module 140 is configured to receive a charging input from the charger. The power management module 141 is configured to connect to the battery 142, the charging management module 140, and the processor 110. The power management module 141 receives an input from the battery 142 and/or the charging management module 140, and supplies power to the processor 110, the internal memory 121, the display 194, the camera 193, the wireless communications module 160, and the like. The power management module 141 may be further configured to monitor parameters such as a battery capacity, a battery cycle count, and a battery health status (electric leakage or impedance). In some other embodiments, the power management module 141 may alternatively be disposed in the processor 110. In some other embodiments, the power management module 141 and the charging management module 140 may alternatively be disposed in a same device.

A wireless communication function of the electronic device 800 may be implemented through the antenna 1, the antenna 2, the mobile communications module 150, the wireless communications module 160, the modem processor, the baseband processor, and the like.

The antenna 1 and the antenna 2 are configured to: transmit and receive electromagnetic wave signals. Each antenna in the electronic device 800 may be configured to cover one or more communication bands. Different antennas may be further multiplexed, to improve antenna utilization. For example, the antenna 1 may be multiplexed as a diversity antenna in a wireless local area network. In some other embodiments, an antenna may be used in combination with a tuning switch.

The mobile communications module 150 can provide a solution, applied to the electronic device 800, to wireless communication including 2G, 3G, 4G, 5G, and the like. The wireless communications module 160 may provide a solution, applied to the electronic device 800, to wireless communication including a wireless local area network (wireless local area network, WLAN) (for example, a wireless fidelity (wireless fidelity, Wi-Fi) network), Bluetooth (Bluetooth, BT), a global navigation satellite system (global navigation satellite system, GNSS), frequency modulation (frequency modulation, FM), near field communication (near field communication, NFC), infrared (infrared, IR) technology, and the like. The wireless communications module 160 may be one or more components integrating at least one communications processor module. The wireless communications module 160 receives an electromagnetic wave through the antenna 2, performs frequency modulation and filtering processing on an electromagnetic wave signal, and sends a processed signal to the processor 11o. The wireless communications module 160 may further receive a to-be-sent signal from the processor 110, perform frequency modulation and amplification on the signal, and convert the signal into an electromagnetic wave for radiation through the antenna 2.

In some embodiments, the electronic device 800 can be communicatively connected to the band 100 by using the mobile communications module 150 or the wireless communications module 160.

In some embodiments, in the electronic device 800, the antenna 1 and the mobile communications module 150 are coupled, and the antenna 2 and the wireless communications module 160 are coupled, so that the electronic device 800 can communicate with a network and another device by using a wireless communications technology. The wireless communications technology may include a global system for mobile communications (global system for mobile communications, GSM), a general packet radio service (general packet radio service, GPRS), code division multiple access (code division multiple access, CDMA), wideband code division multiple access (wideband code division multiple access, WCDMA), time-division code division multiple access (time-division code division multiple access, TD-SCDMA), long term evolution (long term evolution, LTE), BT, a GNSS, a WLAN, NFC, FM, an IR technology, and/or the like. The GNSS may include a global positioning system (global positioning system, GPS), a global navigation satellite system (global navigation satellite system, GLONASS), a BeiDou navigation satellite system (BeiDou navigation satellite system, BDS), a quasi-zenith satellite system (quasi-zenith satellite system, QZSS), and/or a satellite based augmentation system (satellite based augmentation system, SBAS).

The electronic device 800 implements a display function by using the GPU, the display 194, the application processor, and the like. The GPU is a microprocessor for image processing, and is connected to the display 194 and the application processor. The GPU is configured to: perform mathematical and geometric calculation, and render an image. The processor 110 may include one or more GPUs that execute program instructions to generate or change display information.

The electronic device 800 can implement a photographing function by using ISP, the camera 193, the video codec, GPU, the display 194, the application processor, and the like.

The external memory interface 120 may be configured to connect to an external storage card, for example, a micro SD card, to extend a storage capability of the electronic device 800. The external memory card communicates with the processor 11o through the external memory interface 120, to implement a data storage function. For example, files such as music and videos are stored in the external storage card.

The internal memory 121 may be configured to store computer-executable program code. The executable program code includes instructions. The internal memory 121 may include a program storage area and a data storage area. The program storage area may store an operating system, an application required by at least one function (for example, a voice playing function or an image playing function), and the like. The data storage area may store data (such as audio data and an address book) and the like that are created in a use process of the electronic device 800. In addition, the internal memory 121 may include a high-speed random access memory, and may further include a nonvolatile memory, for example, at least one magnetic disk storage device, a flash memory device, or a universal flash storage (universal flash storage, UFS). The processor 110 runs instructions stored in the internal memory 121 and/or instructions stored in the memory disposed in the processor, to perform various function applications and data processing of the electronic device 800.

The electronic device 800 may implement an audio function such as music playing or recording by using the audio module 170, the speaker 170A, the receiver 170B, the microphone 170C, the headset jack 170D, the application processor, and the like.

The button 190 includes a power button, a volume button, and the like. The button 190 may be a mechanical button, or may be a touch button. The electronic device 800 may receive a button input, and generate a key signal input related to a user setting and function control of the electronic device 800.

The motor 191 may generate a vibration prompt. The motor 191 may be configured to produce an incoming call vibration prompt and a touch vibration feedback. For example, touch operations performed on different applications (for example, a photographing application and an audio playing application) may correspond to different vibration feedback effects. The motor 191 may also correspond to different vibration feedback effects for touch operations performed on different areas of the display 194. Different application scenarios (for example, time reminding, information receiving, an alarm clock, and a game) may also correspond to different vibration feedback effects. A touch vibration feedback effect may be further customized.

The indicator 192 may be an indicator light, and may be configured to indicate a charging status and a power change, or may be configured to indicate a message, a missed call, a notification, and the like.

The SIM card interface 195 is configured to connect to a SIM card.

Figure 9:
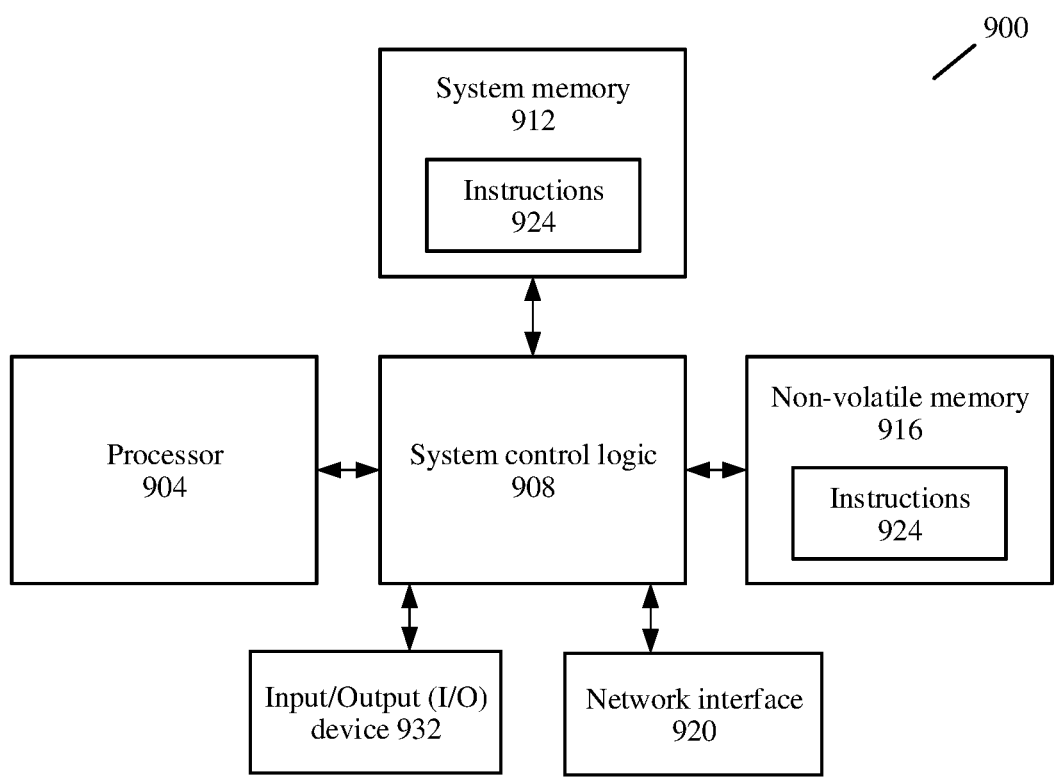
FIG. 9 is a block diagram of an electronic device according to some embodiments of this application.

FIG. 9 shows a block diagram of a structure of an electronic device 900 that can implement a function of the electronic device 200 shown in FIG. 1 according to an embodiment of this invention. In an embodiment, the electronic device 900 may include one or more processors 904, system control logic 908 connected to at least one of the processors 904, system memory 912 connected to the system control logic 908, a nonvolatile memory (NVM) 916 connected to the system control logic 908, and a network interface 920 connected to the system control logic 908.

In some embodiments, the processor 904 may include one or more single-core or multi-core processors. In some embodiments, the processor 904 may include any combination of a general-purpose processor and a dedicated processor (for example, a graphics processing unit, an application processor, or a baseband processor). In an embodiment in which the electronic device 900 uses an eNB (Evolved NodeB, enhanced NodeB) or a RAN (Radio Access Network, radio access network) controller, the processor 904 may be configured to perform various conforming embodiments, for example, one or more of the plurality of embodiments described above.

In some embodiments, the system control logic 908 may include any proper interface controller, to provide any proper interface for the at least one of the processors 904 and/or any proper device or component that communicates with the system control logic 908.

In some embodiments, the system control logic 908 may include one or more memory controllers, to provide an interface connected to the system memory 912. The system memory 912 may be configured to: load and store data and/or instructions. In some embodiments, the memory 912 in the electronic device 900 may include any proper volatile memory, for example, a proper dynamic random access memory (DRAM).

The NVM/memory 916 may include one or more tangible non-transitory computer-readable media that are configured to store data and/or instructions. In some embodiments, the NVM/memory 916 may include any proper nonvolatile memory such as a flash memory and/or any proper nonvolatile storage device such as at least one of an HDD (Hard Disk Drive, hard disk drive), a CD (Compact Disc, compact disc) drive, and a DVD (Digital Versatile Disc, digital versatile disc) drive.

The NVM/memory 916 may include some storage resources on an apparatus installed on the electronic device 900, or may be accessed by a device, but is not necessarily a part of the device. For example, the NVM/memory 916 may be accessed over a network through the network interface 920.

In particular, the system memory 912 and the NVM/memory 916 each may include a temporary copy and a permanent copy of an instruction 924. The instruction 924 may include an instruction that enables, when executed by at least one of the processor 904, the electronic device 900 to implement the method shown in FIG. 3A to FIG. 3C to FIG. 7. In some embodiments, the instruction 924, hardware, firmware, and/or software components thereof may additionally/alternatively be deployed in the system control logic 908, the network interface 920, and/or the processor 904.

The network interface 920 may include a transceiver, and is configured to provide a radio interface for the electronic device 900 to communicate with any other proper device (for example, a front-end module or an antenna) through one or more networks. In some embodiments, the network interface 920 may be integrated into another component of the electronic device 900. For example, the network interface 920 may be integrated into at least one of the system memory 912, the NVM/memory 916, and a firmware device (not shown) having instructions in the processor 904. When the at least one of the system memory 912, the NVM/ memory 916, and the firmware device (not shown) having instructions in the processor 904 executes the instructions, the electronic device 900 implements the methods shown in FIG. 3A to FIG. 3C to FIG. 7.

The network interface 920 may further include any proper hardware and/or firmware to provide a multiple-input and multiple-output radio interface. For example, the network interface 920 may be a network adapter, a wireless network adapter, a phone modem, and/or a wireless modem.

In an embodiment, at least one of the processors 904 may be packaged together with logic of one or more controllers used for the system control logic 908 to form a system in package (SiP). In an embodiment, at least one of the processors 904 may be integrated on a same tube core with logic of one or more controllers used for the system control logic 908, to form a system on a chip (SoC).

The electronic device 900 may further include an input/output (I/O) device 932. The I/O device 932 may include a user interface, so that a user can interact with the electronic device 900. A design of a peripheral component interface enables a peripheral component to also interact with the electronic device 900. In some embodiments, the electronic device 900 further includes a sensor. The sensor is configured to determine at least one of an environmental condition and location information that are related to the electronic device 900.

In some embodiments, the user interface may include but is not limited to a display (for example, a liquid crystal display or a touchscreen display), a speaker, a microphone, one or more cameras (for example, a still image camera and/or a video camera), a flashlight (for example, a light-emitting diode flashlight), and a keyboard.

In some embodiments, the peripheral component interface may include but is not limited to a nonvolatile memory port, an audio jack, and a charging port.

In some embodiments, the sensor may include but is not limited to a gyro sensor, an accelerometer, a proximity sensor, an ambient light sensor, and a positioning unit. The positioning unit may alternatively be a part of the network interface 920, or may interact with the network interface 920, to communicate with a component (for example, a global positioning system (GPS) satellite) in a positioning network.

Reference to "an embodiment" or "an embodiment" in this specification means that specific features, structures, or characteristics described with reference to the embodiments are included in at least one example implementation solution or technology according to this disclosure. In the specification, the phrases "in an embodiment" do not necessarily all represent a same embodiment.

The disclosure also relates to an apparatus for performing operations in the text. The apparatus may be constructed specifically for the required purpose or may include a general purpose computer selectively activated or reconfigured by a computer program stored in the computer. Such a computer program may be stored in a computer-readable medium, for example, but not limited to any type of disk, including a floppy disk, an optical disc, a CD-ROM, a magneto-optical disc, a read-only memory (ROM), a random access memory (RAM), an EPROM, an EEPROM, a magnetic or optical card, an application-specific integrated circuit (ASIC), or any type of medium that is suitable for storing electronic instructions, and each may be coupled to a computer system bus. In addition, the computer mentioned in the specification may include a single processor or may use an architecture involving a plurality if processors for increased computing power.

The processes and displays presented herein are not inherently related to any specific computer or other apparatus. Various general purpose systems may also be used in conjunction with programs taught herein, or it may be proved convenient to construct more specialized apparatuses to perform one or more method steps. Structures for the various systems are discussed in the following description. In addition, any specific programming language sufficient to implement the technologies and implementations of this disclosure may be used. Various programming languages may be used to implement this disclosure, as discussed in this specification.

In addition, the language used in the present specification has been primarily chosen for readability and instructional purposes and may not be chosen to depict or limit the disclosed subject matter. Therefore, this disclosure is intended to illustrate rather than limit the scope of the concepts discussed herein.

What is claimed is:

1. A method for controlling an electronic device to perform photoplethysmography detection comprising:
   obtaining historical detection data of a sensor of the electronic device, wherein the sensor is a photoplethysmography sensor disposed in the electronic device, the photoplethysmography sensor comprises a plurality of light sources and at least one photoelectric sensing element, and each light source has a corresponding photoelectric sensing element;
   calculating a confidence of the historical detection data;
   determining, based on the calculated confidence of the historical detection data, whether a light source to be turned on by the photoplethysmography sensor in a next detection time segment comprises a light source different from a light source turned on when the historical detection data is obtained; and
   determining that a photoelectric sensing element to be turned on in the next detection time segment is a photoelectric sensing element corresponding to the determined light source to be turned on.

2. The method according to claim 1, wherein obtaining the historical detection data of the photoplethysmography sensor comprises:
   obtaining detection data from the photoplethysmography sensor in a detection time segment closest in time to the next detection time segment.

3. The method according to claim 1, wherein calculating the confidence of the historical detection data comprises:
   calculating, based on the historical detection data, a probability that a detected event occurs to a user of the electronic device; and
   calculating the confidence of the historical detection data based on the probability that the detected event occurs to the user, wherein if the probability that the detected event occurs to the user is closer to 0 or 1, the confidence is higher.

4. The method according to claim 3, wherein calculating, based on the historical detection data, the probability that the detected event occurs to the user of the electronic device comprises calculating, by using the following formula, the probability that the detected event occurs to the user:

$$p=1/(1+e^{\hat{}}(-\alpha \hat{}\ Tf)); \text{ and}$$

wherein calculating the confidence of the historical detection data based on the probability that the detected event occurs to the user comprises calculating, by using the following formula, the confidence of the historical detection data:

$$c=2\times abs(0.5-p),$$

wherein c is a confidence calculation result, f is a feature related to atrial fibrillation detection, α is a weight matrix corresponding to the feature related to atrial fibrillation detection, e is the base of the natural logarithm, and p represents a possibility that the data is atrial fibrillation.

5. The method according to claim 1, wherein determining, based on the calculated confidence of the historical detection data, whether a light source to be turned on by the photoplethysmography sensor in a next detection time segment comprises a light source different from a light source turned on when the historical detection data is obtained comprises:
   determining whether the confidence of the historical detection data is greater than a predetermined threshold; and
   determining, based on the calculated confidence being greater than the predetermined threshold, that the light source to be turned on by the photoplethysmography sensor in the next detection time segment comprises only the light source turned on when the historical detection data is obtained; or
   determining, based on the confidence not being greater than the predetermined threshold, that the light source to be turned on by the photoplethysmography sensor in the next detection time segment comprises the light source turned on when the historical detection data is obtained and the different light source.

6. The method according to claim 1, further comprising:
   obtaining regular information, wherein the regular information comprises at least one of user information, motion information, and a current measurement time of the electronic device, and wherein the user information comprises at least one of physical health information, age information, and gender information of the user.

7. The method according to claim 6, wherein determining, based on the calculated confidence of the historical detection data, whether a light source to be turned on by the photoplethysmography sensor in a next detection time segment comprises a light source different from a light source turned on when the historical detection data is obtained comprises:
   determining, based on the regular information and the confidence of the historical detection data, whether the light source to be turned on by the photoplethysmography sensor in the next detection time segment comprises the light source different from the light source turned on when the historical detection data is obtained.

8. The method according to claim 6, further comprising:
   determining whether an initialization condition of the photoplethysmography sensor is met; and
   determining, based on the regular information if the initialization condition is met, an initial light source and an initial photoelectric sensing element that are to be turned on by the photoplethysmography sensor.

9. The method according to claim 8, wherein the initialization condition comprises any one of the following:
   the electronic device is used by the user for a first time;
   a time point for switching between a day mode and a night mode of the photoplethysmography sensor is reached; and
   the electronic device performs a data update.

10. The method according to claim 8, wherein determining, based on the regular information if the initialization condition is met, the initial light source and the initial photoelectric sensing element that are to be turned on by the photoplethysmography sensor comprises:
    calculating, by using the following formulas, a quantity of initial light sources to be turned on by the photoplethysmography sensor:

$$r=1/(1+e^{\wedge}(-\theta^{\wedge}Tx));\text{ and}$$

$$b=\text{Ceil}(r\times n);$$

wherein r represents a health risk such that a higher value of r indicates a higher health risk of the user, x is a vector that represents a health risk parameter, θ is a matrix that represents a weight of impact of the health risk parameter on health, e is the base of the natural logarithm, b represents a calculated quantity of light sources to be turned on, and n represents a maximum quantity of light sources supported by the device; and
   determining that the initial photoelectric sensing element to be turned on is a photoelectric sensing element corresponding to the determined initial light source to be turned on.

11. A method for photoplethysmography detection, the method comprising:
    obtaining, by a first electronic device, historical detection data of a photoplethysmography sensor from a second electronic device, wherein the second electronic device comprises a photoplethysmography sensor, the photoplethysmography sensor comprises a plurality of light sources and at least one photoelectric sensing element, and each light source has a corresponding photoelectric sensing element;
    calculating, by the first electronic device, a confidence of the historical detection data;
    determining, by the first electronic device based on the calculated confidence of the historical detection data, whether a light source to be turned on by the photoplethysmography sensor of the second electronic device in a next detection time segment comprises a light source different from a light source turned on when the historical detection data is obtained;
    determining, by the first electronic device, that a photoelectric sensing element to be turned on by the photoplethysmography sensor of the second electronic device in the next detection time segment is a photoelectric sensing element corresponding to the determined light source to be turned on; and
    sending, by the first electronic device to the second electronic device, information about the light source to be turned on and information about the photoelectric sensing element to be turned on.

12. The method according to claim 11, wherein obtaining, by the first electronic device, the historical detection data of the photoplethysmography sensor from the second electronic device comprises:
    obtaining, by the first electronic device from the second electronic device, detection data detected by the photoplethysmography sensor of the second electronic device in a detection time segment closest in time to the next detection time segment of the second electronic device.

13. The method according to claim 11, wherein calculating, by the first electronic device, the confidence of the historical detection data comprises:
    calculating, by the first electronic device based on the historical detection data, a probability that a detected event occurs to a user of the electronic device; and calculating, by the first electronic device, the confidence of the historical detection data based on the probability that the detected event occurs to the user, wherein if the probability that the detected event occurs to the user is closer to 0 or 1, the confidence is larger.

14. The method according to claim 11, wherein determining, by the first electronic device based on the calculated confidence of the historical detection data, whether a light source to be turned on by the photoplethysmography sensor in a next detection time segment comprises a light source different from a light source turned on when the historical detection data is obtained comprises:
determining, by the first electronic device, whether the confidence of the historical detection data is greater than a predetermined threshold; and
determining, based on the confidence being greater than the predetermined threshold, by the first electronic device, that the light source to be turned on by the photoplethysmography sensor in the next detection time segment comprises only the light source turned on when the historical detection data is obtained; or
determining, based on the confidence not being greater than the predetermined threshold, by the first electronic device, that the light source to be turned on by the photoplethysmography sensor in the next detection time segment comprises the light source turned on when the historical detection data is obtained and the different light source.

15. The method according to claim 11, further comprising:
obtaining, by the first electronic device, regular information, wherein the regular information comprises at least one of user information, motion information, and a current measurement time of the electronic device, and wherein the user information comprises at least one of physical health information, age information, and gender information of the user.

16. The method according to claim 15, wherein the determining, by the first electronic device based on the calculated confidence of the historical detection data, whether a light source to be turned on by the photoplethysmography sensor in a next detection time segment comprises a light source different from a light source turned on when the historical detection data is obtained comprises:
determining, by the first electronic device, based on the regular information and the confidence of the historical detection data, whether the light source to be turned on by the photoplethysmography sensor in the next detection time segment comprises the light source different from the light source turned on when the historical detection data is obtained.

17. The method according to claim 15, further comprising:
determining, by the first electronic device, whether an initialization condition of the photoplethysmography sensor is met; and
determining, by the first electronic device, based on the regular information if the initialization condition is met, an initial light source and an initial photoelectric sensing element that are to be turned on by the photoplethysmography sensor.

18. The method according to claim 17, wherein the initialization condition comprises any one of the following:
the electronic device is used by the user for a first time;
a time point for switching between a day mode and a night mode of the photoplethysmography sensor is reached; and
the electronic device performs a data update.

19. An electronic device, comprising:
one or more processors;
a photoplethysmography sensor, wherein the photoplethysmography sensor comprises a plurality of light sources and at least one photoelectric sensing element, and wherein each light source has a corresponding photoelectric sensing element; and
a non-transitory computer-readable storage medium storing a program to be executed by the one or more processors, the program including instructions for:
obtaining historical detection data of the photoplethysmography sensor;
calculating a confidence of the historical detection data;
determining, based on the calculated confidence of the historical detection data, whether a light source to be turned on by the photoplethysmography sensor in a next detection time segment comprises a light source different from a light source turned on when the historical detection data is obtained; and
determining that a photoelectric sensing element to be turned on in the next detection time segment is a photoelectric sensing element corresponding to the determined light source to be turned on.

20. The electronic device according to claim 19, wherein the electronic device is further enabled to perform:
obtaining detection data detected by the photoplethysmography sensor in a detection time segment closest in time to the next detection time segment.

* * * * *